United States Patent [19]
Bandman et al.

[11] Patent Number: 6,124,116
[45] Date of Patent: Sep. 26, 2000

[54] RAB PROTEINS

[75] Inventors: Olga Bandman, Mountain View; Janice Au-Young, Berkeley, both of Calif.

[73] Assignee: Incyte Pharmaceuticals, Inc., Palo Alto, Calif.

[21] Appl. No.: 08/741,411

[22] Filed: Oct. 29, 1996

[51] Int. Cl.⁷ ............................ C12P 21/06; C07H 21/04
[52] U.S. Cl. .................. 435/69.1; 536/23.2; 536/24.3; 530/350; 435/325; 435/70.1
[58] Field of Search ................... 536/23.2, 24.3, 536/24.31; 530/350; 435/325, 70.1, 69.1

[56] References Cited

FOREIGN PATENT DOCUMENTS 9514772   1/1995   WIPO .

OTHER PUBLICATIONS

Khosravi–Far R et al., "Isoprenoid modification of rab proteins terminating in CC or CXC motifs," 1991, *Proc. Natl. Acad. Sci.* 88:6264–6268.

Seabra, MC et al., "Deficient Geranylgeranylation of Ram/Rab27 in Choroideremia," 1996, *J. Biol. Chem.* 270:24420–24427.

Seabra, MC et al., "Retinal Degeneration in Choroideremia: Deficiency of Rab Geranylgeranyl Transferase," 1993, *Science* 259:377–381.

Zahraoui, A. et al., "The Human Rab Genes Encode a Family of GTP–binding Proteins Related to Yeast YPT1 and SEC4 Products Involved in Secretion," 1989, *J. Biol. Chem.* 264:12394–123401.

Fridell RA et al., "Nuclear export of late HIV–1 mRNAs occurs via a cellular protein export pathway," 1996, *Proc. Natl. Acad. Sci.* 93:4421–4424.

Tuomikoski, T. et al., "Inhibition of endocytic vesicle fusion in vitro by the cell–cycle control protein kinase cdc2," 1989, *Nature* 342:942–945.

Olkkonen, V et al., "Molecular cloning and subcellular localization of three GTP–binding proteins of the rab subfamily," 1993, *Journal of Cell Science*, 106:1249–1261 (GI 437987).

Shimizu, H et al. (GI 206543) GenBank Sequence Database (Accession 206543), National Center for Biotechnology Information, National Library of Medicine, Bethesda, Maryland, 2084.

Brauers, A et al., "Alternative mRNA splicing of the novel GTPase Rab28 generates isoforms with different C–termini," *Eur. J. Biochem.* 237:833–840.

Wilson, D.B., "Identification and subcellular localization of human rab5b, a new member of the ras related superfamily of GTPases," *Journal of Clinical Investigation*, vol. 89, pp. 996–1005, XP002057689, 1992.

Chen, D., et al., "Molecular cloning of two novel rab genes from human melanocytes," *Gene*, vol. 174, 129–134, XP002057690, Sep. 1996.

Bao, X., et al., "Low MR GTP–binding protein RAB31" Homo Sapiens, *EMBL Database, Heidelberg, DE AC: Q13636*, XP002057691, Jan. 10, 1996.

Hillier, L., et al., yz73g12.r1 Homo sapiens cDNA clone 288742 5' similar to PIR:S40208 rab22 protein—dog., *EST*, XP002057692, May 4, 1996.

Burgess et al. J. Cell Biol. (1990) 11:2129–2138.

Lazar et al. Mol. Cell Biol. (1988) 8:1247–1252.

Tao et al. J. Immunol. (1989) 143 (8):2595–2601.

Gillies et al. Human Antibod. & Hybridoma 1990 1(1):47–54.

Hillier, L. et al. 1995–Accession Nos. N75242, H71565, N59216, N21210, N33379, WO1927, W24485, N42201, N36775.

Lutcke, A. et al. 1993 J. Cell Biol. 121(3):553–564.

Janoueix–Lerosey, I et al. 1995 J. Biol. Chem. 270(24):14801–14808.

*Primary Examiner*—Lila Feisee
*Assistant Examiner*—Minh-Tam Davis
*Attorney, Agent, or Firm*—Incyte Pharmaceuticals, Inc.

[57] ABSTRACT

The present invention provides four human Rab and Rab-associated proteins (designated collectively as HRAB) and polynucleotides which identify and encode HRAB. The invention also provides genetically engineered expression vectors and host cells comprising the nucleic acid sequences encoding HRAB and a method for producing HRAB. The invention also provides for use of HRAB and agonists, antibodies, or antagonists specifically binding HRAB, in the prevention and treatment of diseases associated with expression of HRAB. Additionally, the invention provides for the use of antisense molecules to polynucleotides encoding HRAB for the treatment of diseases associated with the expression of HRAB. The invention also provides diagnostic assays which utilize the polynucleotide, or fragments or the complement thereof, and antibodies specifically binding HRAB.

9 Claims, 20 Drawing Sheets

```
      9                  18                 27                 36                 45              54
5' CTT TGN TCC GTT TAN CCC GGT TCA GAN GNG CCG CTG AGC TCC GGC ACT GCC TGG 63                 72                 81                 90                 99             108
   CTG CGA GCA CAT GAT GGC GAT ACG GGA GCT CAA AGT GTG CCT TCT CGG GGG ACT 117                126                135                144                153             162
   GAT GGA ACC GAT CTG TTC CCT TAC GAA GTG TCA CAG TAT TGG CAG GAC TCT GGA 171                180                189                198                207             216
   CAA GGA CAA GGA AGG CTG CAT TCC TGT GGC ACC AGG TGG AAG ATG GAG GAC GAC
                                                                         M   E   D   D 225                234                243                252                261             270
   ACT GGG GTT GGG AAA TCA AGC ATC GTG TGT CGA TTT GTC CAG GAT CAC TTT GAC
    T   G   V   G   K   S   S   I   V   C   R   F   V   Q   D   H   F   D 279                288                297                306                315             324
   CAC AAC ATC AGC CCT ACT ATT GGG GCA TCT TTT ATG ACC AAA ACT GTG CCT TGT
    H   N   I   S   P   T   I   G   A   S   F   M   T   K   T   V   P   C 333                342                351                360                369             378
   GGA AAT GAA CTT CAC AAG TTC CTC ATC TGG GAC ACT GCT GGT CAG GAA CGG TTT
    G   N   E   L   H   K   F   L   I   W   D   T   A   G   Q   E   R   F
```

FIGURE 1A

```
                                        387                  396              405                    414                  423            432
CAT TCA TTG GCT CCC ATG TAC TAT CGA GGC TCA GCT GCA GCT GTT ATC GTG TAT
 H   S   L   A   P   M   Y   Y   R   G   S   A   A   A   V   I   V   Y 441                  450              459                    468                  477              486
GAT ATT ACC AAG CAG GAT TCA TTT TAT ACC TTG AAG AAA TGG GTC AAG GAG CTG
 D   I   T   K   Q   D   S   F   Y   T   L   K   K   W   V   K   E   L 495                  504              513                    522                  531              540
AAA GAA CAT GGT CCA GAA AAC ATT GTA ATG GCC ATC GCT GGA AAC AAG TGC GAC
 K   E   H   G   P   E   N   I   V   M   A   I   A   G   N   K   C   D 549                  558              567                    576                  585              594
CTC TCA GAT ATT AGG GAG GTT CCC CTG AAG GAT GCT AAG GAA TAC GCT GAA TCC
 L   S   D   I   R   E   V   P   L   K   D   A   K   E   Y   A   E   S 603                  612              621                    630                  639              648
ATA GGT GCC ATC GTG GTT GAG ACA AGT GCA AAA AAT GCT ATT AAT ATC GAA GAG
 I   G   A   I   V   V   E   T   S   A   K   N   A   I   N   I   E   E 657                  666              675                    684                  693              702
CTC TTT CAA GGA ATC AGC CGC CAG ATC CCA CCC TTG GAC CCC CAT GAA AAT GGA
 L   F   Q   G   I   S   R   Q   I   P   P   L   D   P   H   E   N   G 711                  720              729                    738                  747              756
AAC AAT GGA ACA ATC AAA GTT GAG AAG CCA ACC ATG CAA GCC AGC CGC CGG TGC
 N   N   G   T   I   K   V   E   K   P   T   M   Q   A   S   R   R   C
```

FIGURE 1B

```
      765              774              783              792              801              810
TGT TGA CCC AAG GCC CGT GGT CCA CGG TAC TTG AAG AAG CCA GAG CCC ACA TCC
 C 819              828              837              846
TGT GCA CTG CTG AAG GAC CCT ACN GCT CCT CGG TGG CCT 3'
 C   A   L   L   K   D   P   T   A   P   R   W   P
```

FIGURE 1C

```
5' CTG CGC TTC CCT GGT CAG GCA CGG CAC GTC TGG CCG GCC GCC AGG ATG CAG GCC
                9          18          27          36          45          54
   L   R   F   P   G   Q   A   R   H   V   W   P   A   A   R   M   Q   A

CCG CAC AAG GAG CAC CTG TAC AAG CGC TAC CAC CAG CTC GTG CTG GAC GTG GGS
                63          72          81          90          99         108
   P   H   K   E   H   L   Y   K   R   Y   H   Q   L   V   D   L   V   G

AAG ACC AGY ATC ATC AAG CGC TTC GCC TAC CGT CTC CAC CAG CTC TCC TAC CGG
               117         126         135         144         153         162
   K   T   S   I   I   K   R   Y   A   Y   R   L   H   Q   L   S   Y   R

GCC ACC ATC GGG GTG GAC TTC GCC CTC AAG GTC CTC AAC TGG GAC AGC AGG ACT
               171         180         189         198         207         216
   A   T   I   G   V   D   F   A   L   K   V   L   N   W   D   S   R   T

CTG GTG CGC CTG CAG CTG TGG GAC ATC GCG GGG CAG GAG CGA TTT GGC AAC ATG
               225         234         243         252         261         270
   L   V   R   L   Q   L   W   D   I   A   G   Q   E   R   F   G   N   M

ACC CGA GTA TAC TAC AAG GAA GCT GTT GGT GCT TTT GTA GTC TTT GAT ATA TCA
               279         288         297         306         315         324
   T   R   V   Y   Y   K   E   A   V   G   A   F   V   V   F   D   I   S

AGA AGT TCC ACA TTT GAG GCA GTC TTA AAA TGG AAA AGT GAT CTG GAT AGT AAA
               333         342         351         360         369         378
   R   S   S   T   F   E   A   V   L   K   W   K   S   D   L   D   S   K
```

FIGURE 2A

```
GTT CAT CTT CCA AAT GGC AGC CCT ATC CCT GCT GTC CTC TTG GCT AAC AAA TGT    432
 V   H   L   P   N   G   S   P   I   P   A   V   L   L   A   N   K   C

441
GAC CAG AAC AAG GAC AGT AGC CCT TCC CAG GTG GAC TTC TGC AAA                486
 D   Q   N   K   D   S   S   P   S   Q   V   D   F   C   K

495
GAA CAT GGC TTT GCC GGA TGG TTT GAA ACC TCT GCA AAG GAT AAC ATA            540
 E   H   G   F   A   G   W   F   E   T   S   A   K   D   N   I

549
GAG GCT GCC CGG TTC CTA GTG GAG AAG ATT CTT GTA AAC CAC CAA AGC TTT        594
 E   A   A   R   F   L   V   E   K   I   L   V   N   H   Q   S   F

603
CCT AAT GAA GAA AAC AAA ATT AAG CTA GAT CAA GAG ACC TTG AGA                648
 P   N   E   E   N   K   I   K   L   D   Q   E   T   L   R

657
GCA GAG AAC AAA TCC CAG TGT TGC TGA TAT ATG GCT TCT GCT TCT CTT GTG TGT    702
 A   E   N   K   S   Q   C   C

711
GCC TCA GCT CTG AAG AAG TTC CTG AAG TTC AGA ATG GGT TAC AGA TGT CAT GTN AGC TGG  756
```

FIGURE 2B

```
         765         774         783         792         801         810
GAG TCT TCC NAC ATG TGG NAC TTC AAA AGG CAG CAC NAC TGG GCG CNT GCA CTT
         819         828         837         846         855         864
ATT TGA AAA TGG AAC TTT GGG AGA AGT ATC CCT GCT ANT GGC TCT GTA ACT TAA
         873         882
CAG ATG ACA ATT AGG CTT TTG TNA 3'
```

FIGURE 2C

```
5' GCC TGC GGA GGG AAG CAA ACC TTC CCC TGG ACC AGA GAG AGG AAG CGG AGA
                9           18          27          36          45          54

CAG GTA GCA ACG CTG TGG ACT GGT GAT GAC AGG AGG ACC TTC AGC CTG CAA GTG
             63          72          81          90          99         108
                                              M

ACC GGG CCT GGG GAA CAG GGC ATG GCA CAG GCA CAC AGG ACC CCC CAG CCC AGG
            117         126         135         144         153         162
                              A   Q   A   H   R   T   P   Q   P   R

GCT GCC CCC AGC CAG CCC CGT GTG TTC AAG CTG GTT CTC CTG GGA AGT GGC TCC
            171         180         189         198         207         216
 A   A   P   S   Q   P   R   V   F   K   L   V   L   L   G   S   G   S

GTG GGT GCG TTC TTC ACA AAG GAG GTG GAT GTG GCC ACC TCT CTG AAG CTT
            225         234         243         252         261         270
 V   G   A   F   F   T   K   E   V   D   V   A   T   S   L   K   L

GAG ATC TGG GAC ACA GCT GGC CAG GAG AAG TAC CAC AGC GTC TGC CAC CTC TAC
            279         288         297         306         315         324
 E   I   W   D   T   A   G   Q   E   K   Y   H   S   V   C   H   L   Y

TTC AGG GGT GCC AAC GCT GCG CTT CTG GTG TAC GAC ATC ACC AGG AAG GAT TCC
            333         342         351         360         369         378
 F   R   G   A   N   A   A   L   L   V   Y   D   I   T   R   K   D   S
```

FIGURE 3A

```
              387                396          405          414          423          432
TTC CTC AAG GCT CAG CAG TGG CTG AAG GAC CTG GAG GAG CAC CCA GGA
 F   L   K   A   Q   Q   W   L   K   D   L   E   E   H   P   G 441                450          459          468          477          486
GAA GTC CTG GTG ATG CTG GTG GGC AAC AAG ACG GAC CTC AGC CAG GAG CGG GAG
 E   V   L   V   M   L   V   G   N   K   T   D   L   S   Q   E   R   E 495                504          513          522          531          540
GTG ACC TTC CAG GAA GGG AAA TTT GCC GAC AGC CAG AAG TTG CTG TTC ATG
 V   T   F   Q   E   G   K   F   A   D   S   Q   K   L   L   F   M 549                558          567          576          585          594
GAA ACT TCG GCC AAA CTG CAG AAC CAC CAG GTG TCG GAG GTG TTC AAT ACA GTG GCC
 E   T   S   A   K   L   Q   N   H   Q   V   S   E   V   F   N   T   V   A 603                612          621          630          639          648
CAA GAG CTA CTG CAG AGA AGC GAC GAG GAG GGC CAG GCT CTA CGG GGG GAT GCA
 Q   E   L   L   Q   R   S   D   E   E   G   Q   A   L   R   G   D   A 657                666          675          684          693          702
GCT GTG GCT CTG AAC AAG GGG CCC GCG AGG CAG GCC AAA TGC TGC GCC CAC TAG
 A   V   A   L   N   K   G   P   A   R   Q   A   K   C   C   A   H 711                720          729          738          747          756
GTG CAG CCA CTC CTG GGG GCT GTG GGG AAG ACA NCC CCT GCC TGG GCC ATG GCC
```

FIGURE 3B

```
     765        774        783        792        801        810
AGC TCT AGG TGG ATT CTG ATT CAC TGT CAA TGC TGG GTT GCT CCC GAG CCC TAG

ATG TTC CT 3'
```

```
                     9            18           27           36           45           54
5' GGG TAC         CGG GCT        GGT TAC      AGC AGC      TCT ACC      CCT CAC      GAC GCA      AAC ATG      GCA GCG
                                                                                                      M          A   A 63           72           81           90           99          108
   CAG AAG        GAC CAG       CAG AAA       GAT GCC      GAG GCG      GAA GGG      CTG AGC      GGC ACG      ACC CTG
    Q   K          D   Q         Q   K         D   A        E   A        E   G        L   S        G   T        T   L 117          126          135          144          153          162
   CTG CCG        AAG CTG       ATT CCC       TCC GGT      GCA GGC      CGG GAG      TGG CTG      GAG CGG      CGC
    L   P          K   L         I   P         S   G        A   G        R   E        W   L        E   R        R 171          180          189          198          207          216
   GCG ACC        ATC CGC       CCT GGA       GCA CCT      TCG TGG      ACC AGC      AGC GCT      TCT CAC      GGC CCC
    A   T          I   R         P   G         A   P        S   W        T   S        S   A        S   H        G   P 225          234          243          252          261          270
   GCA ACC        TGG GAG       AGC TGT       GCC AGC      GCT GTA      CGC AAC      GTG GAG      TAC TAC      CAG AGC
    A   T          W   E         S   C         A   S        A   V        R   N        V   E        Y   Y        Q   S 279          288          297          306          315          324
   AAC TAT        GTG TTC       GTG TTC       CTG GGC      CTC ATC      CTG TAC      TGT GTG      ACG TCC      CCT
    N   Y          V   F         V   F         L   G        L   I        L   Y        C   V        V   T        S   P 333          342          351          360          369          378
   ATG TTG        CTG GTG       GCT GTC       CTG GCT      GTC TTT      TTC GGC      GCC TGT      TAC ATT      CTC TAT CTG
    M   L          L   V         A   V         L   A        V   F        F   G        A   C        Y   I        L   Y   L
```

FIGURE 4A

```
            387      396      405      414      423      432
        CGC ACC TTG GAG TCC AAG CTT GTG CTC TTT GGC CGA GAG GTG AGC CCA GCG CAT
         R   T   L   E   S   K   L   V   L   F   G   R   E   V   S   P   A   H 441      450      459      468      477      486
        CAG TAT GCT CTG GCT GGA GGC ATC TCC TTC CCC TTC TTC TGG CTG GCT GGT GCG
         Q   Y   A   L   A   G   G   I   S   F   P   F   F   W   L   A   G   A 495      504      513      522      531      540
        GGC TCG GCC GTC TTC TGG GTG CTG GGA GCC ACC CTG GTG GTC ATC GGC TCC CAC
         G   S   A   V   F   W   V   L   G   A   T   L   V   V   I   G   S   H 549      558      567      576      585      594
        GCT GCC TTC CAC CAG ATT GAG GCT GTG GAC GGG GAG CTG CAG ATG GAA CCC
         A   A   F   H   Q   I   E   A   V   D   G   E   L   Q   M   E   P 603      612      621      630      639      648
        GTG TGA GGT GTC TTC TGG GAC CTG CCG GCC TCC CGG GCC AGC TGC CCC ACC CCT
         V 657      666      675      684      693      702
        GCC CAT GCC TGT CCT GCA CGG STC TGC TCG TGC TCG GGC CCA CAG CGC CGT CCC ATC 711      720      729      738      747      756
        ACA AGC CCG GGG AGG GAT CCC GCC TTT RAA AAT AAA GCT GTT ATG GGT GTC ATT
        C 3'
```

|  |  |  |  |  |  |  |  |  |  |  |  |  |  |  |  |  |  |  |  |  |
|---|---|---|---|---|---|---|---|---|---|---|---|---|---|---|---|---|---|---|---|---|
| 1 | M | E | - | - | - | - | - | - | - | - | - | - | - | - | - | - | - | - | D T G V G K S S I V C R F V | SEQ ID NO-1 |
| 1 | M | A | L | R | E | - | - | - | - | - | - | - | - | - | - | - | - | - | D T G V G K S S I V W R F V | GI 437987 |
| 1 | M | Q | - | - | - | - | - | - | - | - | - | - | - | - | - | - | - | - | D L G V G K T S I I K R Y V | SEQ ID NO-3 |
| 1 | M | Q | - | - | - | - | - | - | - | - | - | - | - | - | - | - | - | - | D L G V G K T S I I K R Y V | GI 206543 |
| 1 | M | A | Q | - | - | A H R T P Q P R A A P S Q P R V F K L V L L G S G S V G | - | - | - | - | SEQ ID NO-5 |
| 1 | M | A | Q | A A A G L P Q A A S T A S G Q P Y V S K L V L L G S S V G K T S L A L R Y M | GI 297157 |
| 17 | Q D H F D H N I S P T I G A S F M T K T V P C G N E | - | L H K F L I W D T A G Q E | SEQ ID NO-1 |
| 27 | E D S F D P N I N P T I G A S F M T K T V Q Y Q N E | - | L H K F L I W D T A G Q E | GI 437987 |
| 31 | H Q L F S Q H Y R A T I G V D F A L K V L N W D S R T L V R L Q L W D I A G Q E | SEQ ID NO-3 |
| 31 | H Q N F S S H Y R A T I G V D F A L K V L H W D P E T V V R L Q L W D I A G Q E | GI 206543 |
| 32 | - | - | - | - | - | - | A F F T K E V D V G A T | - | S L K L E I W D T A G Q E | SEQ ID NO-5 |
| 41 | K | D F S | - | N V L P T V G C A F F T K V L D L G S S | - | S L K L E I W D T A G Q E | GI 297157 |
| 56 | R F H S L A P M Y Y R G S A A A I V Y D I T K Q D S F Y T L K K W V K E L K E | SEQ ID NO-1 |
| 66 | A F R A L A P M Y Y R G S A A A I H V Y D I T K E E T F S T L K N W V K E L R Q | GI 437987 |
| 71 | R F G N M T R V Y Y K E A V G A F V F D I S R S S T F E A V L K W K S D L D S | SEQ ID NO-3 |
| 71 | R F G N M T R V Y Y R E A M G A F I V E D V T R P A T F E A V A K W K N D L D S | GI 206543 |
| 57 | K Y H S V C H L Y F R G A N A A L L V Y D I T R K D S F L K A Q Q W L K D L E E | SEQ ID NO-5 |
| 79 | K Y Q S V C H L Y F R G A N A A L L V Y D I T R K D S F H K A Q Q W L E D L E K | GI 297157 |

FIGURE 5B

| Pos | Sequence | ID |
|---|---|---|
| 96 | H - G P E N - - - I V M A I A G N K C D L S D I R E V P L K D A K E Y A E - S I | SEQ ID NO-1 |
| 106 | H - G P P N - - - I V V A I A G N K C D L I D V R E V M E R D A K D Y A D - S I | GI 437987 |
| 111 | K V H L P N G S P I P A V L L A N K C D - - - Q N K D S - S Q S P S Q V D Q F C K | SEQ ID NO-3 |
| 111 | K L T L P N G K P V S V V L A N K C D - - - Q G K D V L V N N G L K M D Q F C K | GI 206543 |
| 97 | E L H P G E - - - V L V M L V G N K T D L S Q E R E V T F Q E G K E F A D - S Q | SEQ ID NO-5 |
| 119 | E F Q P G E - - - V V V M L V G N K T D L G E E R E V T F Q E G K E F A E - S K | GI 297157 |
| 131 | G A I V V - - - E T S A K N A I N I E E L F Q G I S R Q I - - - P P L D P H E | SEQ ID NO-1 |
| 141 | H A I F V - - - E T S A K N A I N I N E L F I E I S R R I I - - P S A D A N P | GI 437987 |
| 148 | E H G F A G W F E T S A K D N I N I E E A A R F L V E K I L V N H Q S F P N E - | SEQ ID NO-3 |
| 149 | E H G F V G W F E T S A K E N I N I D E A S R C L V K H I L A N E C D F I E S I | GI 206543 |
| 133 | K L L F M - - - E T S A K L N H Q V S E V F N T V A Q E L L Q R S D E E G Q A L | SEQ ID NO-5 |
| 155 | S L L F M - - - E T S A K L N Y Q V S E I F N T V A Q E L L Q R A G D T G S S R | GI 297157 |
| 164 | N G N N G T I K V E K P T M Q A S R R C C | SEQ ID NO-1 |
| 174 | P S G K G F K L R R Q S E P Q R S C C | GI 437987 |
| 187 | E N D V D K I K L D Q E T L R A E N K S Q C C | SEQ ID NO-3 |
| 189 | E P D I V K P H L T S P K V V S C S G C A K S | GI 206543 |
| 170 | R G D A - A V A L N K G P A - R Q A K C C A H | SEQ ID NO-5 |
| 192 | P Q E G E A V A L N Q E P P I R Q R Q C C A R | GI 297157 |

```
  1   MAAQKDQQKDAEAEGLSGTTLLPKLIPSGAGREWLERRRA            SEQ ID NO-7
  1   ---HEDQQKDAEGEGLSATTLLPKLIPSGAGREWLEQAPG            GI 722667

41   TIRP-GAPSWTSSASHGPATWESCASA-VRNVEYYQSNYV            SEQ ID NO-7
 38   DHPALGHLSWTSNVSRDPAMWESFASAWYGTVEYYQSNYV            GI 722667

79   FVFLGLILYCVVTSPMLLVALAVFFGACYILYLRTLESKL            SEQ ID NO-7
 78   FVFLGLILYCVVTSPMLLVALAVFF                           GI 722667

119   VLFGREVSPAHQYALAGGISFPFFWLAGAGSAVFWVLGAT            SEQ ID NO-7
102                                                       GI 722667

159   LVVIGSHAAFHQIEAVDGEEELQMEPV                         SEQ ID NO-7
102                                                       GI 722667
```

FIGURE 6

RAB PROTEINS

FIELD OF THE INVENTION

This invention relates to nucleic acid amino acid sequences of a novel human Rab and Rab-associated proteins and to the use of these sequences in the diagnosis, prevention, and treatment of choroideremia, AIDS, and cancer.

BACKGROUND OF THE INVENTION

Transport of material between the different subcellular compartments of eukaryote cells often requires carrier vesicles, which bud from a donor organelle and fuse with the recipient one. Rab proteins are low molecular weight guanidine triphosphatases (GTPases) of the Ras superfamily which are localized to the membrane surfaces of organelles. They appear to be involved in the regulation of intracellular vesicular transport in both exocytic and endocytic pathways. They may also be involved in the complex and critical processes of organelle fragmentation and restructuring that occur each cell cycle. Rab proteins cycle between active GTP-bound and inactive GDP-bound conformations.

Newly formed Rab proteins associate with Rab escort proteins (REPs) in the cell cytosol. Rab proteins are then stably isoprenylated by the covalent addition of two 20-carbon geranylgeranyl groups to carboxy-terminal cysteine residues (Khosravi-Far R et al (1991) Proc Natl Acad Sci 88: 6264–6268). Prenylation occurs by Rab geranylgeranyl transferase (GGTase) and is essential for Rab protein function and membrane localization. A deficiency in prenylation of one particular Rab leads to choroideremia, a form of retinal degeneration that may cause blindness (Seabra MC et al (1996) J Biol Chem 270: 24420–24427; Seabra et al (1993) Science 259: 377–381). Each of the more than 30 Rab proteins identified appears to have characteristic intracellular distribution and may function in distinct transport events. REPs help transfer newly prenylated Rab proteins to the appropriate organelle membrane.

The amino acid sequence of Rab proteins reveal conserved GTP-binding domains that are characteristic among Ras superfamily members (Zahraoui A et al (1989) J Biol Chem 264: 12394–123401). GTP binding or conversion from GDP to GTP form occurs en route to the organelle membrane. Experimental evidence shows that GTP-bound Rab proteins are directed into nascent transport vesicles where they interact with SNARE factors, a complex of proteins that direct vesicle targeting and fusion. Following vesicle transport, GTPase activating proteins (GAPs) in the target membrane convert Rab proteins to the GDP-bound form. A cytosolic protein, guanine-nucleotide dissociation inhibitor (GDI) helps return GDP-bound Rab proteins to their membrane of origin.

Rab proteins appear to play a role in mediating the function of a viral gene, Rev, which is essential for replication of HIV-1, the virus responsible for AIDS (Flavell RA et al (1996) Proc Natl Acad Sci 93: 4421–4424). Rab proteins, when overexpressed, can significantly enhance Rev function. Furthermore, mutational analysis suggests that Rev protein has a nuclear signal domain that is necessary for localization into the cell nucleus and is likely to be a Rab protein binding site (Flavell et al, supra).

Both the inhibition of vesicle transport and organelle fragmentation during mitosis are due to an inhibition of vesicle fusion, which occurs while vesicle budding continues. Protein phosphorylation by Cdc2 protein kinase is a key regulatory event in mitosis. Toumikoski T et al has shown that addition of Cdc2 protein kinase to interphase cell extracts inhibits vesicle fusion (1989, Nature 342: 942–945). Furthermore, low GTP-gamma-S concentrations, which are likely to block Rab protein GTPase activity, inhibit the fusion reaction, suggesting that Rab proteins could be mediating this critical cell cycle event. Loss of cell cycle control is a key characteristic of all human cancers.

The discovery of additional Rab and Rab-associated genes and the proteins encoded provides potential agents which are more effective than currently available therapeutic agents in the diagnosis and treatment of choroideremia, AIDS, and cancer. Thus, the new Rab and Rab-associated proteins would satisfy a need in the art by providing new means for the diagnosis, prevention, or treatment of choroideremia, AIDS, and cancer.

SUMMARY OF THE INVENTION

The present invention features novel Rab and Rab-associated proteins hereinafter designated individually as HRABA, HRABB, HRABC, HRABD, and collectively as HRAB and characterized as having homology to Rab and Rab-associated proteins and intracellular transport activity.

Accordingly, the invention features substantially purified Rab and Rab-associated proteins HRABA, HRABB, HRABC, and HRABD, having intracellular transport activity and as shown in amino acid sequences of SEQ ID NOS: 1, 3, 5, and 7, respectively.

One aspect of the invention features isolated and substantially purified polynucleotides that encode HRABA, HRABB, HRABC, and HRABD. In a particular aspect, the polynucleotides are the nucleotide sequences of SEQ ID NOS: 2, 4, 6, and 8, respectively.

The invention also relates to a polynucleotide sequences comprising the complement of SEQ ID NOS: 2, 4, 6, and 8 or variants thereof. In addition, the invention features polynucleotide sequences which hybridize under stringent conditions to SEQ ID NOS: 2, 4, 6, and 8.

The invention additionally features nucleic acid sequences encoding polypeptides, oligonucleotides, peptide nucleic acids (PNA), fragments, portions or antisense molecules thereof, and expression vectors and host cells comprising polynucleotides that encode HRAB. The present invention also features antibodies which bind specifically to HRAB, and pharmaceutical compositions comprising substantially purified HRAB. The invention also features the use of agonists and antagonists of HRAB.

BRIEF DESCRIPTION OF THE FIGURES

FIGS. 1A, 1B, and 1C shows the amino acid sequence (SEQ ID NO:1) and nucleic acid sequence (SEQ ID NO:2) of HRABA. The alignment was produced using MACDNASIS PRO software (Hitachi Software Engineering Co., Ltd, San Bruno, Calif.).

FIGS. 2A, 2B, and 2C shows the amino acid sequence (SEQ ID NO:3) and nucleic acid sequence (SEQ ID NO:4) of HRABB.

FIGS. 3A, 3B, 3C shows the amino acid sequence (SEQ ID NO:5) and nucleic acid sequence (SEQ ID NO:6) of HRABC.

FIGS. 4A and 4B shows the amino acid sequence (SEQ ID NO:7) and nucleic acid sequence (SEQ ID NO:8) of HRABD.

FIGS. 5A and 5B shows the amino acid sequence alignments among HRABA (SEQ ID NO:1), canine rab22 (GI 437987; SEQ ID NO:9), HRABB (SEQ ID NO:3), rat Rab-related GTP-binding protein (GI 206543; SEQ ID NO:10), HRABC (SEQ ID NO:5), and mouse Rab17 (GI 297157; SEQ ID NO:11). The alignment was produced using the multisequence alignment program of DNASTAR software (DNASTAR Inc, Madison Wis.).

FIG. 6 shows the amino acid sequence alignments between HRABD (SEQ ID NO:7) and mouse Rab6/Rab5-associated protein (GI 722667; SEQ ID NO:12).

DESCRIPTION OF THE INVENTION

Figure 7:
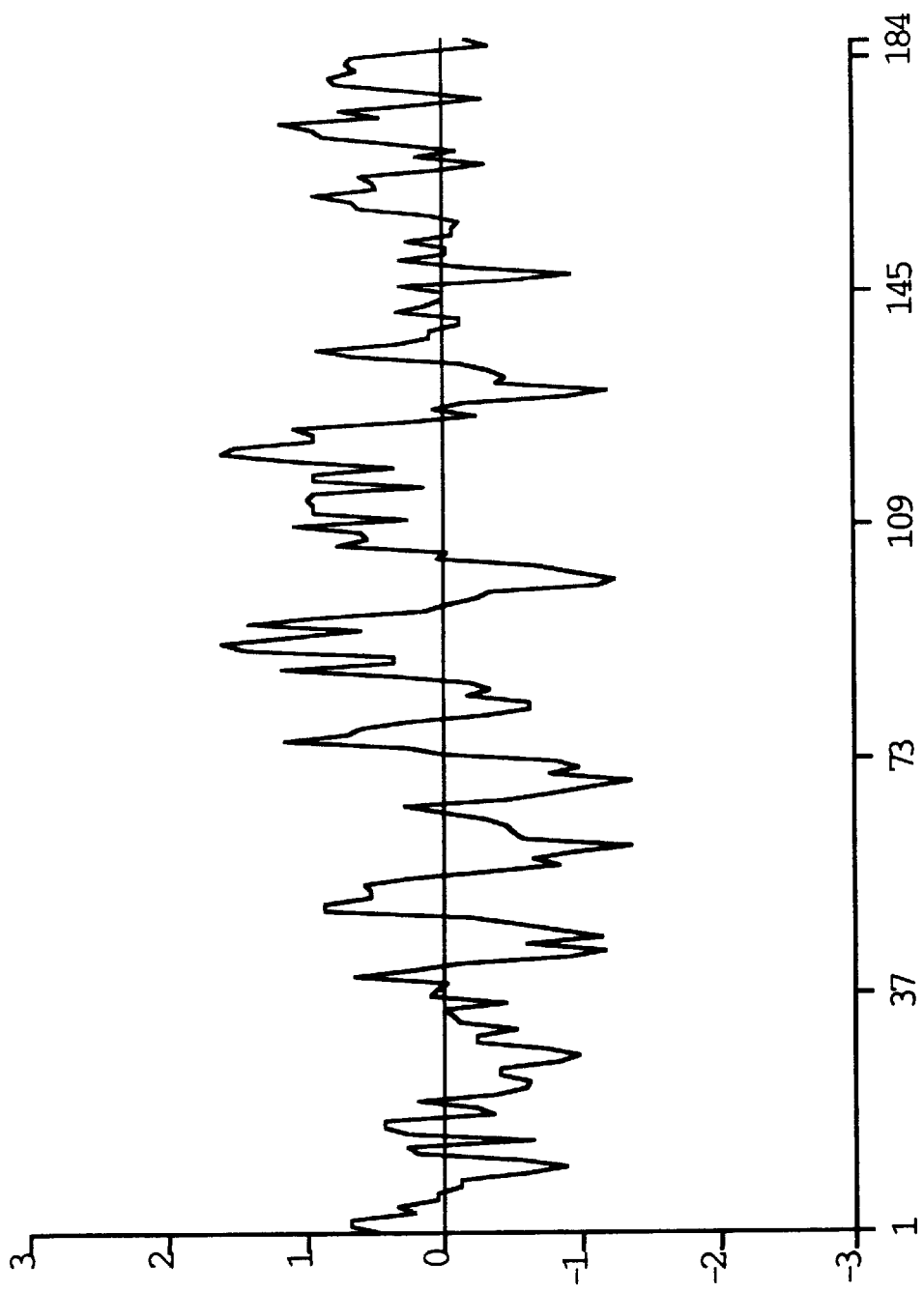
FIG. 7 shows the hydrophobicity plot (generated using MACDNASIS PRO software) for HRABA, SEQ ID NO:1). The positive X axis reflects amino acid position, and the negative axis reflects hydrophobicity (FIGS. 7, 8, 9, 10, 11, and 12). Similarily.

Before the present protein, nucleotide sequence, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single-or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen et al. (1993) Anticancer Drug Des. 8:53–63).

HRAB, as used herein, refers to the amino acid sequences of substantially purified HRAB obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR (Perkin Elmer, Norwalk, Conn.) in the 5' and/or the 3' direction and resequenced, or which has been assembled from the overlapping sequences of more than one Incyte clone using the GCG fragment assembly system (GCG, Madison, Wis.), or which has been both extended and assembled.

A "variant" of HRAB, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HRAB, or any oligopeptide thereof, to induce a specific immune response in appropriate animals or cells and to bind with specific antibodies.

The term "agonist", as used herein, refers to a molecule which, when bound to HRAB, causes a change in HRAB which modulates the activity of HRAB. Agonists may include proteins, nucleic acids, carbohydrates, or any other molecules which bind to HRAB.

The terms "antagonist" or "inhibitor", as used herein, refer to a molecule which, when bound to HRAB, blocks the biological or immunological activity of HRAB. Antagonists and inhibitors may include proteins, nucleic acids, carbohydrates, or any other molecules which bind to HRAB.

The term "modulate", as used herein, refers to a change or an alteration in the biological activity of HRAB. Modulation may be an increase or a decrease in protein activity, a change in binding characteristics, or any other change in the biological, functional or immunological properties of HRAB.

The term "mimetic", as used herein, refers to a molecule, the structure of which is developed from knowledge of the structure of HRAB or portions thereof and, as such, is able to effect some or all of the actions of Rab or Rab-associated protein-like molecules.

The term "derivative", as used herein, refers to the chemical modification of a nucleic acid encoding HRAB or the encoded HRAB. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) PCR Primer. a Laboratory Manual, Cold Spring Harbor Press, Plainview, N.Y.).

The term "hybridization", as used herein, refers to any process by which a strand of nucleic acid bonds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1,3,5, or 7" encompasses the full-length human HRAB and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but are not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to is elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HRAB or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is complementary to SEQ ID NO:2, 4, 6, or 8 by northern analysis is indicative of the presence of mRNA encoding HRAB in a sample and thereby correlates with expression of the transcript from the polynucleotide encoding the protein.

"Alterations" in the polynucleotide of SEQ ID NO:2, 4, 6, or 8, as used herein, comprise any alteration in the sequence of polynucleotides encoding HRAB including deletions, insertions, and point mutations that may be detected using hybridization assays. Included within this definition is the detection of alterations to the genomic DNA sequence which encodes HRAB (e.g., by alterations in the pattern of restriction fragment length polymorphisms capable of hybridizing to SEQ ID NO:2, 4, 6, or 8), the inability of a selected fragment of SEQ ID NO:2, 4, 6, or 8 to hybridize to a sample of genomic DNA (e.g., using allele-specific oligonucleotide probes), and improper or unexpected hybridization, such as hybridization to a locus other than the normal chromosomal locus for the polynucleotide sequence encoding HRAB (e.g., using fluorescent in situ hybridization [FISH] to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind HRAB polypeptides can be prepared using intact polypeptides or fragments containing small peptides of interest as the immunizing antigen. The polypeptide or peptide used to immunize an animal can be derived from translated cDNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of Rab and Rab-associated proteins HRAB, the polynucleotides encoding HRAB, and the use of these compositions for the diagnosis, prevention, or treatment of choroideremia, AIDS, and cancer.

Nucleic acids encoding the human HRABA of the present invention were first identified in CDNA, Incyte Clone 334674 from the eosinophil cDNA library EOSIHET02 through a computer-generated search for amino acid sequence alignments. A consensus sequence, SEQ ID NO:2, was derived from the following overlapping and/or extended nucleic acid sequences (derived from the stated cDNA library): Incyte Clones 334674 (EOSIHET02), 125981 (LUNGNOT01), 1370809 (BSTMNON02), and 1420225 (KIDNNOT09).

Figure 10:
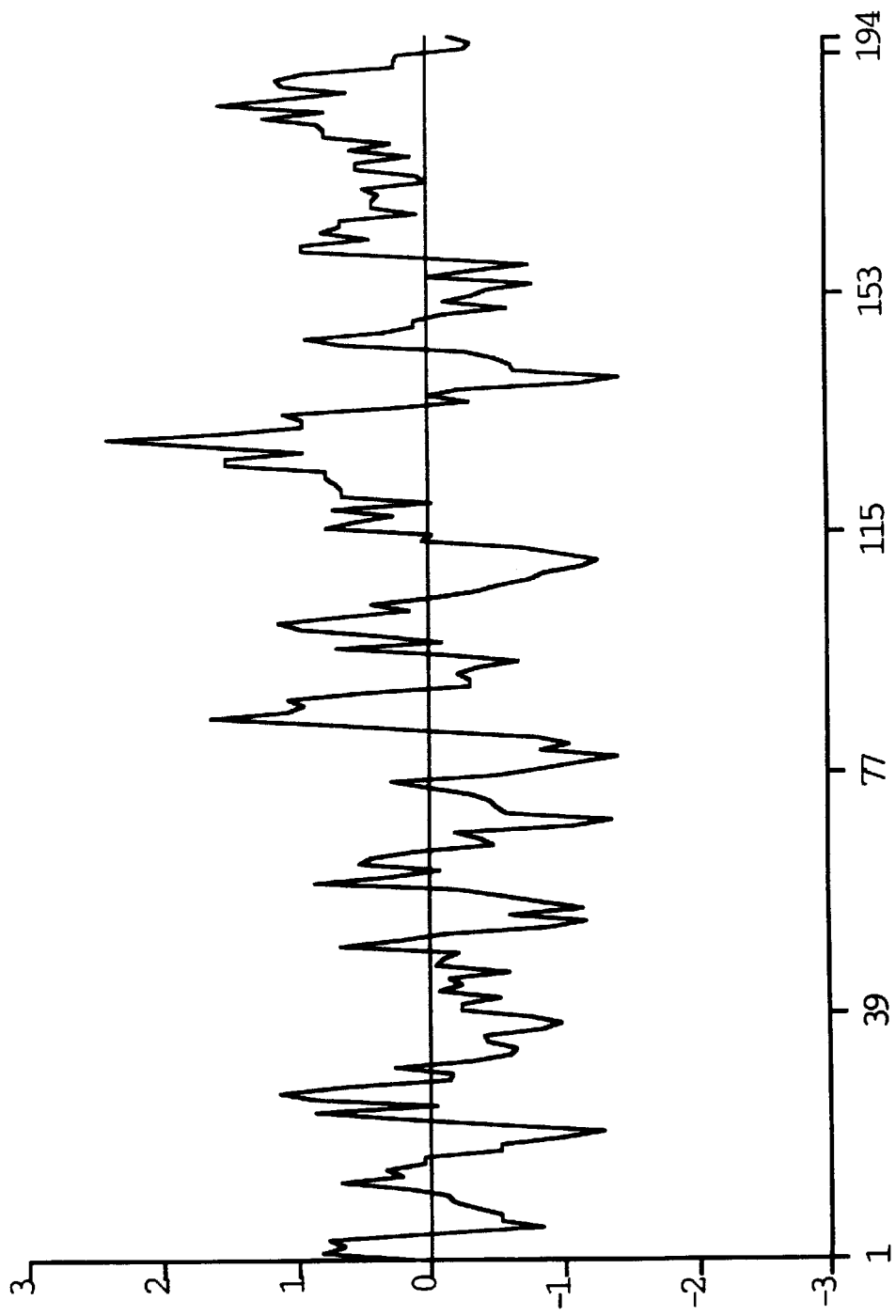
FIG. 10 shows the hydrophobicity plot for canine rab22 (SEQ ID NO:9)

In one embodiment, the invention encompasses a Rab protein (HRABA), a polypeptide comprising the amino acid sequence of SEQ ID NO:1, as shown in FIGS. 1A, 1B, and 1C. HRABA is 184 amino acids in length. HRABA has chemical and structural homology with canine rab22 (GI 437987; SEQ ID NO:9), rat Rab-related GTP-binding protein (GI 206543; SEQ ID NO:10), and mouse Rab17 (GI 297157; SEQ ID NO:11; FIGS. 5A and 5B)). In particular, HRABA and canine rab22 share 68% identity. As illustrated by FIGS. 7 and 10, HRABA and canine rab22 have similar hydrophobicity which suggests that they have a similar structure. The homology includes conserved GTP/GDP binding domains and carboxy-terminal cysteine residues that are suitable substrates for prenylation (FIGS. 5A and 5B). HRABA has two potential N-glycosylation sites.

Nucleic acids encoding the human HIRABB of the present invention were first identified in cDNA, Incyte Clone 367194 from the synovial tissue cDNA library SYN-ORAT01 through a computer-generated search for amino acid sequence alignments. A consensus sequence, SEQ ID NO:4, was derived from the following overlapping and/or extended nucleic acid sequences (derived from the stated cDNA library): Incyte Clones 367194 (SYNORAT01), 874099 (LUNGAST01), 1214370 (BRSTTUT01), 1320737 (BLADNOT04), 1452285 (PENITUT01), and 1489006 (UCMCL5T01).

Figure 8:
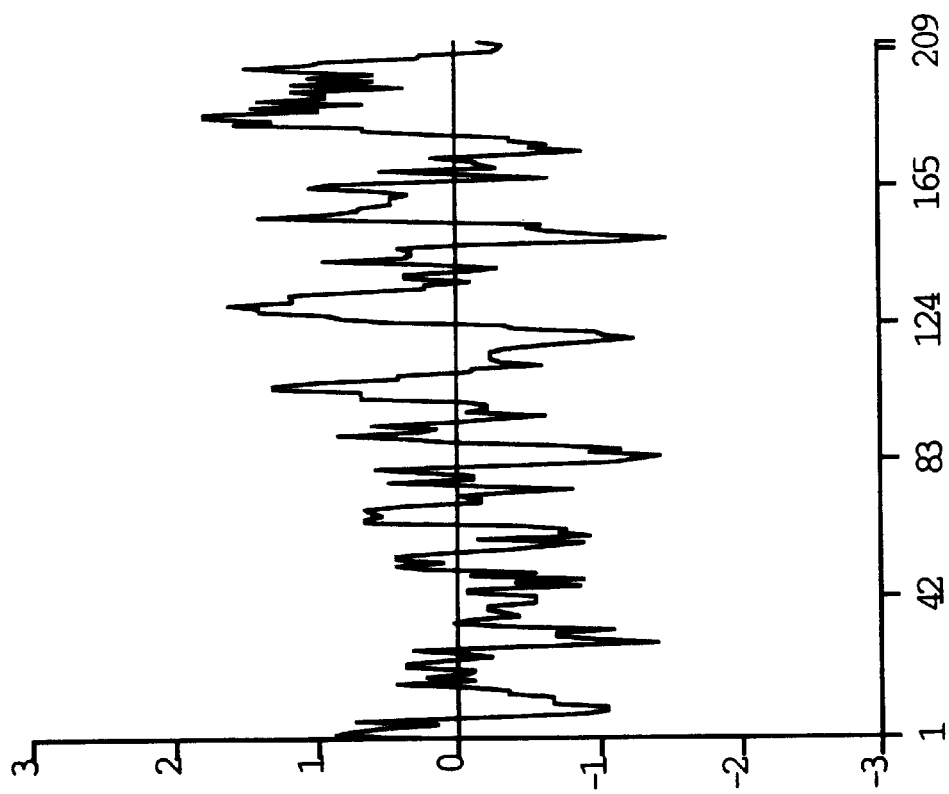
FIG. 8 shows the hydrophobicity plot for HRABB (SEQ ID NO:3)

In one embodiment, the invention encompasses a Rab protein (HRABB), a polypeptide comprising the amino acid sequence of SEQ ID NO:3, as shown in FIG. 2. HRABB is 209 amino acids in length. HRABB has chemical and structural homology with canine rab22 (GI 437987; SEQ ID NO:9), rat Rab-related GTP-binding protein (GI 206543; SEQ ID NO:10), and mouse Rab17 (GI 297157; SEQ ID NO:11; FIGS. 5A and 5B)). In particular, HRABB and canine rab22 share 70% identity. As illustrated by FIGS. 8 and 10, HRABB and canine rab22 have similar hydrophobicity which suggests that they have a similar structure. The homology includes conserved GTP/GDP binding domains and carboxy-terminal cysteine residues that are suitable substrates for prenylation (FIGS. 5A and 5B). HRABB has three potential N-glycosylation sites.

Nucleic acids encoding the human HRABC of the present invention were first identified in cDNA, Incyte Clone 1272054 from the testicular tumor cDNA library TESTTUT02 through a computer-generated search for amino acid sequence alignments. A consensus sequence, SEQ ID NO:6, was derived from the following overlapping and/or extended nucleic acid sequences (derived from the stated cDNA library): Incyte Clones 1272054 (TESTTUT02) and 601225 (BRSTNOT02).

Figure 9:
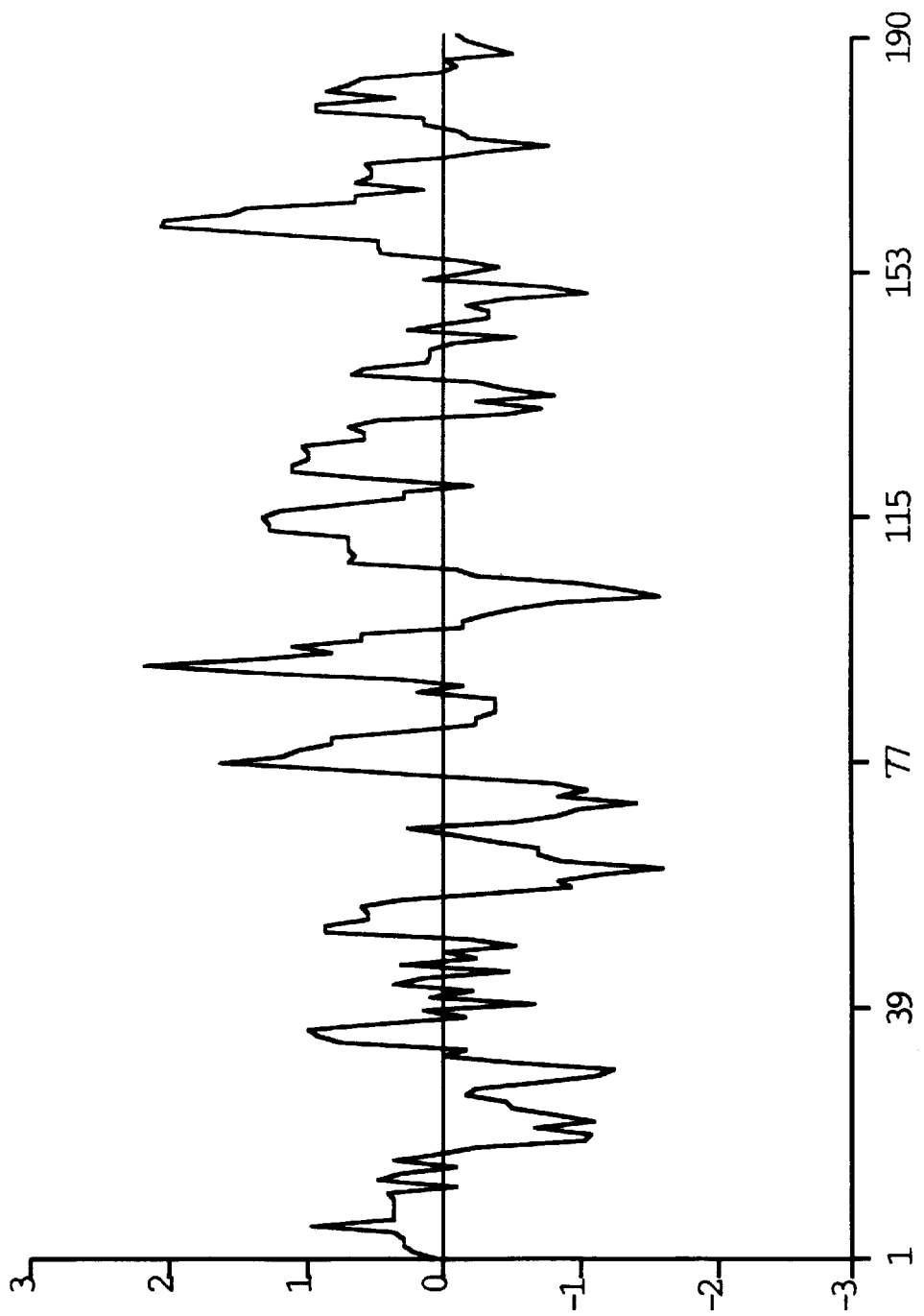
FIG. 9 shows the hydrophobicity plot for HRABC (SEQ ID NO:5)

In one embodiment, the invention encompasses a Rab protein (HRABC), a polypeptide comprising the amino acid sequence of SEQ ID NO:5, as shown in FIGS. 3A, 3B, and 3C. HRABC is 190 amino acids in length. HRABC has chemical and structural homology with canine rab22 (GI 437987; SEQ ID NO:9), rat Rab-related GTP-binding protein (GI 206543; SEQ ID NO:10), and mouse Rab17 (GI 297157; SEQ ID NO:11; FIGS. 5A and 5B)). In particular, HRABC and canine rab22 share 75% identity. As illustrated by FIGS. 9 and 10, HRABC and canine rab22 have similar hydrophobicity which suggests that they have a similar structure. The homology includes conserved GTP/GDP binding domains and carboxy-terminal cysteine residues that are suitable substrates for prenylation (FIG. 5). HRABC has two potential N-glycosylation sites.

Nucleic acids encoding the human HRABD of the present invention were first identified in cDNA, Incyte Clone 358844 from the synovial tissue cDNA library SYNORAB01 through a computer-generated search for amino acid sequence alignments. A consensus sequence, SEQ ID NO:8, was derived from the following overlapping and/or extended nucleic acid sequences (derived from the stated cDNA library): Incyte Clones 358844 (SYNORAB01), 235332 (SINTNOT02), 761131 (BRAITUT02), and 966344 (BRSTNOT05).

Figure 11:
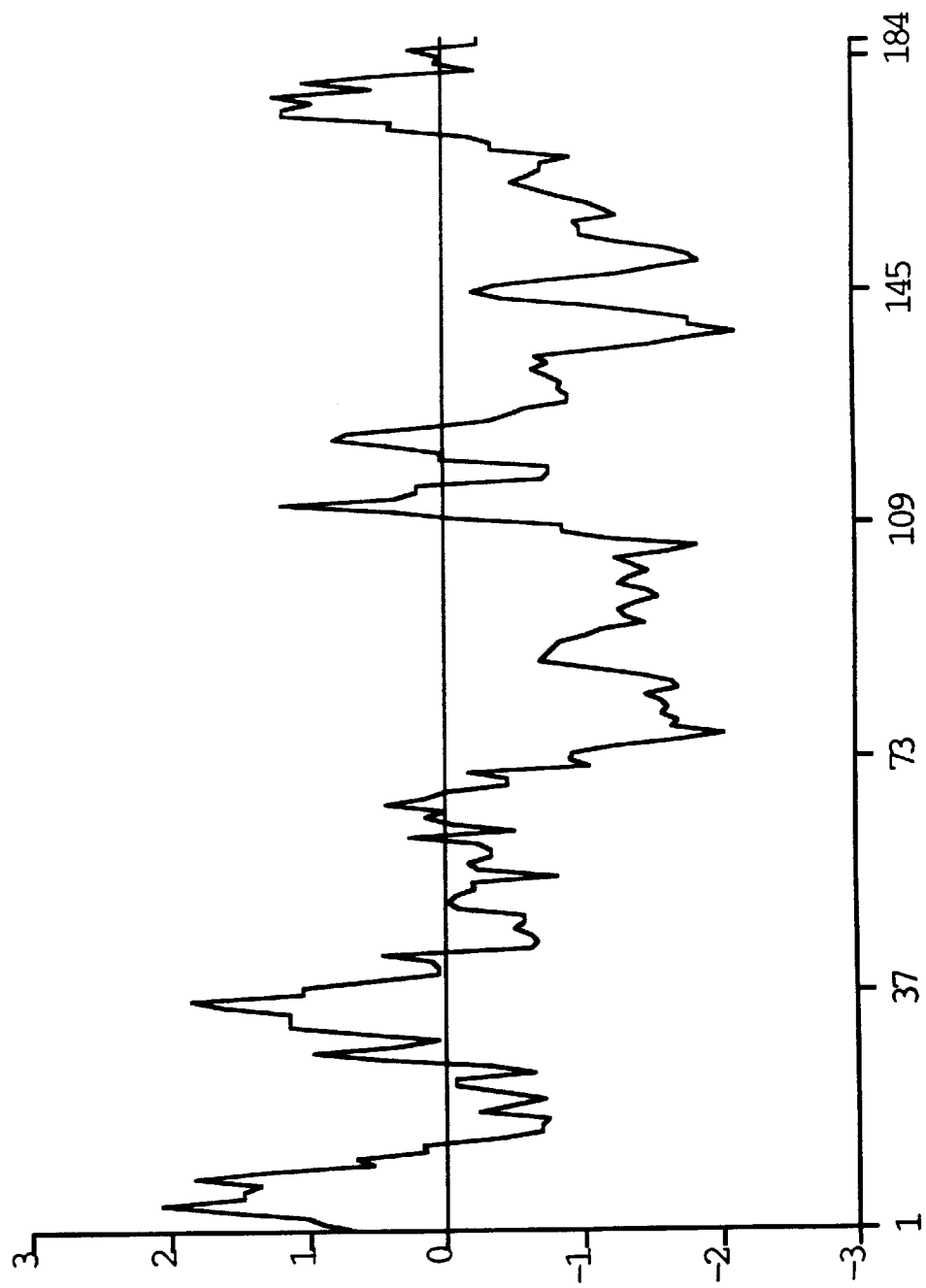
FIG. 11 shows the hydrophobicity plot for HRABD (SEQ ID NO:7)
Figure 12:
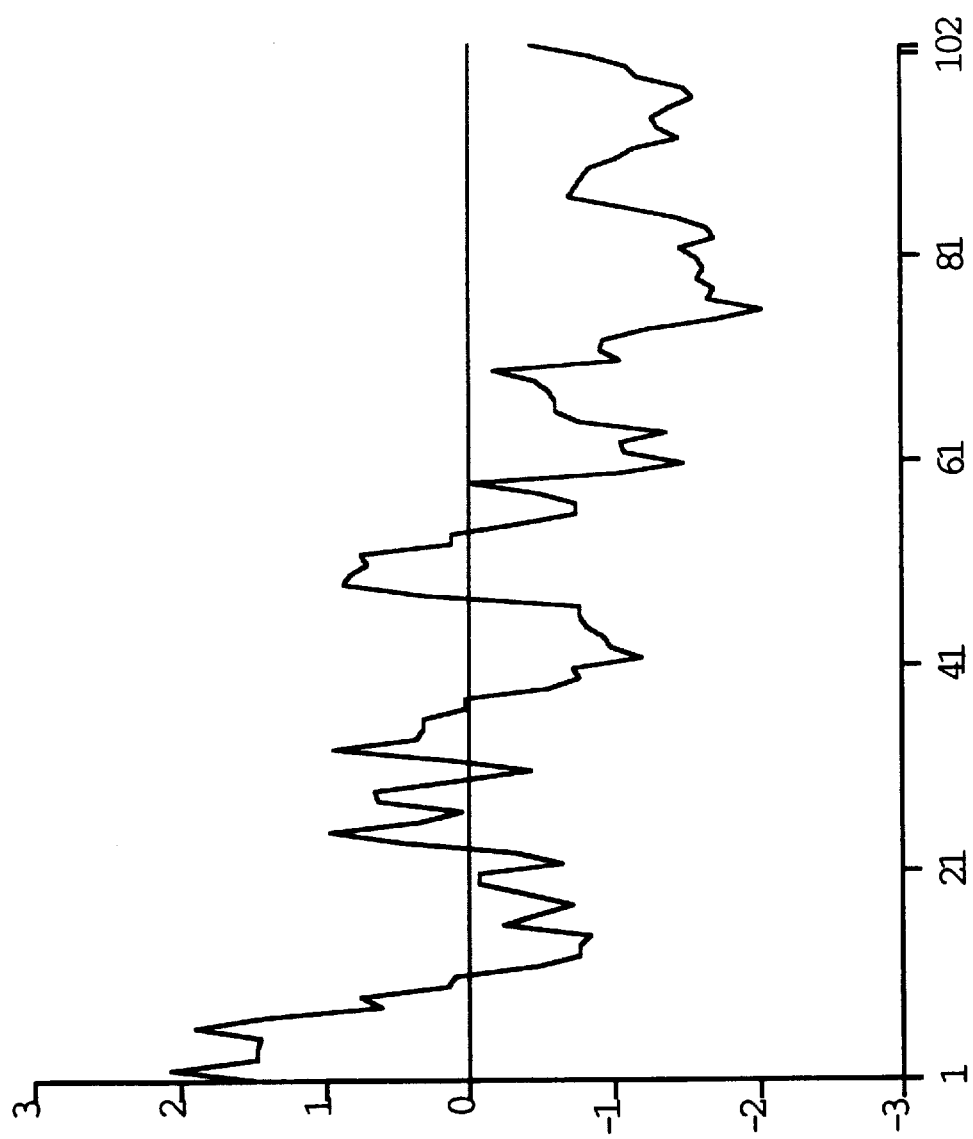
FIG. 12 shows the hydrophobicity plot for mouse Rab6/Rab5-associated protein (SEQ ID NO:12).

In one embodiment, the invention encompasses a Rab protein (HRABD), a polypeptide comprising the amino acid sequence of SEQ ID NO:7, as shown in FIGS. 4A and 4B. HRABD is 184 amino acids in length. HRABD has chemical and structural homology with mouse Rab6/Rab5-associated protein (GI 722667; SEQ ID NO:12). In particular, HRABD and Rab6/Rab5-associated protein share 77% identity. As illustrated by FIGS. 11 and 12, HRABD and Rab6/Rab5-associated protein have similar hydrophobicity which suggests that they have a similar structure.

The invention also encompasses HRAB variants. A preferred HRAB variant is one having at least 80%, and more preferably 90%, amino acid sequence similarity to the HRAB amino acid sequence (SEQ ID NOS:1, 3, 5, or:7). A most preferred HRAB variant is one having at least 95% amino acid sequence similarity to SEQ ID NOS:1, 3, 5, or 7.

The invention also encompasses polynucleotides which encode HRAB. Accordingly, any nucleic acid sequence which encodes the amino acid sequence of HRAB can be used to generate recombinant molecules which express HRAB. In a particular embodiment, the invention encompasses the polynucleotide comprising the nucleic acid of SEQ ID NOS:2, 4, 6, or 8, as shown in FIGS. 1A,1B,1C, 2A,2B,2C,3A,3B,3C,4A, and 4B.

It will be appreciated by those skilled in the art that as a result of the degeneracy of the genetic code, a multitude of nucleotide sequences encoding HRAB, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HRAB, and all such variations are to be considered as being specifically disclosed.

Although nucleotide sequences which encode HRAB and its variants are preferably capable of hybridizing to the nucleotide sequence of the naturally occurring HRAB under appropriately selected conditions of stringency, it may be advantageous to produce nucleotide sequences encoding HRAB or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HRAB and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HRAB and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HRAB or any portion thereof.

Also encompassed by the invention are polynucleotide sequences that are capable of hybridizing to the claimed nucleotide sequences, and in particular, those shown in SEQ ID NOS:2, 4, 6, or 8, under various conditions of stringency. Hybridization conditions are based on the melting temperature (Tm) of the nucleic acid binding complex or probe, as taught in Berger and Kimmel (1987; Methods Enzymol. Vol. 152), and may be used at a defined stringency.

Altered nucleic acid sequences encoding HRAB which are encompassed by the invention include deletions, insertions, or substitutions of different nucleotides resulting in a polynucleotide that encodes the same or a functionally equivalent HRAB. The encoded protein may also contain deletions, insertions, or substitutions of amino acid residues which produce a silent change and result in a functionally equivalent HRAB. Deliberate amino acid substitutions may be made on the basis of similarity in polarity, charge, solubility, hydrophobicity, hydrophilicity, and/or the amphipathic nature of the residues as long as the biological activity of HRAB is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding HRAB. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the MICROLAB 2200 (Hamilton, Reno, Nev.), Peltier thermal cycler (PTC200; M J Research, Watertown, Mass.), and the ABI 377 DNA sequencers (Perkin Elmer).

The polynucleotide sequences encoding I TRAB may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Gobinda et al. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and may be is useful in finding intron/exon junctions.

When screening for full-length cDNAs, it is preferable to use libraries that have been size-selected to include larger cDNAs. Also, random-primed libraries are preferable in that is they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-translated regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes ,(one for each nucleotide) which are laser activated, and detection of the emitted wavelengths by a charge coupled devise camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HRAB, or fusion proteins or functional equivalents thereof, may be used in recombinant DNA molecules to direct expression of HRAB in appropriate host cells. Due to the inherent degeneracy of the genetic code, other DNA sequences which encode substantially the same or a functionally equivalent amino acid sequence may be produced and these sequences may be used to clone and express HRAB.

As will be understood by those of skill in the art, it may be advantageous to produce HRAB-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HRAB coding sequences for a variety of reasons, including but not limited to, alterations which modify the cloning processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, the natural, modified, or recombinant polynucleotides encoding HRAB may be ligated to a heterologous sequence to encode a fusion protein. For example, to screen peptide libraries for inhibitors of HRAB activity, it may be useful to encode a chimeric HRAB protein that can be recognized by a commercially available antibody. A fusion protein may also be engineered to contain a cleavage site located between a HRAB encoding sequence and the heterologous protein sequence, so that HRAB may be cleaved and purified away from the heterologous moiety.

In another embodiment, the coding sequences of HRAB may be synthesized, in whole or in part, using chemical methods well known in the art (see Caruthers, M. H. et al. (1980) Nucl. Acids Res. Symp. Ser. 215–223, Horn, T. et al.

(1980) Nucl. Acids Res. Symp. Ser. 225–232). Alternatively, the protein itself may be produced using chemical methods to synthesize the HRAB amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431A peptide synthesizer (Perkin Elmer).

The newly synthesized peptide may be substantially purified by preparative high performance liquid chromatography (e.g., Creighton, T. (1983) *Proteins, Structures and Molecular Principles,* W H Freeman and Co., New York, N.Y.). The composition of the synthetic peptides may be confirmed by amino acid analysis or sequencing (e.g., the Edman degradation procedure; Creighton, supra). Additionally, the amino acid sequence of HRAB, or any part thereof, may be altered during direct synthesis and/or combined using chemical methods with sequences from other proteins, or any part thereof, to produce a variant polypeptide.

In order to express a biologically active IIRAB, the nucleotide sequence encoding HRAB or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HRAB coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express a HRAB coding sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HRAB, vectors based on SV40 or EBV may be used with an appropriate selectable marker.

In bacterial systems, a number of expression vectors may be selected depending upon the use intended for HRAB. For example, when large quantities of HRAB are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HRAB may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HRAB may be driven by any of a number of promoters. For example, viral promoters such as the 35S and 19S promoters of CaMV may be used alone or in combination with the omega leader sequence from TMV (Takamatsu et al. (1987) EMBO J. 6:307–311; Brisson et al. (1984) Nature 310:511–514). Alternatively, plant promoters such as the small subunit of RUBISCO or heat shock promoters may be used (Coruzzi et al. (1984) EMBO J. 3:1671–1680; Broglie et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y., pp. 191–196; or Weissbach and Weissbach (1988) *Methods for Plant Molecular Biology*, Academic Press, New York, N.Y.; pp. 421–463).

An insect system may also be used to express HRAB. For example, in one such system, *Autographa californica* nuclear polyhedrosis virus (AcNPV) is used as a vector to express foreign genes in *Spodoptera frugiperda* cells or in Trichoplusia larvae. The sequence encoding HRAB may be cloned into a non-essential region of the virus, such as the polyhedrin gene, and placed under control of the polyhedrin promoter. Successful insertion of HRAB will render the polyhedrin gene inactive and produce recombinant virus lacking coat protein. The recombinant viruses may then be used to infect, for example, *S. frugiperda* cells or Trichoplusia larvae in which HRAB may be expressed (Smith et al. (1983) J. Virol 46:584; Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HRAB may be ligated into an adenovirus transcription/translation complex consisting of the late promoter and tripartite leader sequence. Insertion in a non-essential E1 or E3 region of the viral genome may be used to obtain a viable virus which is capable of expressing HRAB in infected host cells (Logan and Shenk (1984) Proc. Natl. Acad. Sci. 81 :3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HRAB. Such signals include the ATG initiation codon and adjacent sequences. In cases where sequences encoding HRAB, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf D et al. (1994) Results Probl. Cell Differ. 20:125–162; Bittner et al. (1987) Methods Enzymol. 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HRAB may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^{31}$ or $aprt^{31}$ cells, respectively. Also, antimetabolite, antibiotic or herbicide resistance can be used as the basis for selection; for example, dhfr, which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14), and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131). .

Although the presence/absence of marker gene expression suggests that the gene of interest is also present, its presence and expression may need to be confirmed. For example, if the sequences encoding HRAB is inserted within a marker gene sequence, recombinant cells containing sequences encoding HRAB can be identified by the absence of marker gene function. Alternatively, a marker gene can be placed in tandem with a sequence encoding HRAB under the control of a single promoter. Expression of the marker gene in response to induction or selection usually indicates expression of the tandem gene as well.

Alternatively, host cells which contain the coding sequences for HRAB and express HRAB may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of the nucleic acid or protein.

The presence of the polynucleotide sequences encoding HRAB can be detected by DNA—DNA or DNA-RNA hybridization or amplification using probes or portions or fragments of polynucleotides encoding IIRAB. Nucleic acid amplification based assays involve the use of oligonucleotides or oligomers based on the HRAB-encoding sequence to detect transformants containing DNA or RNA encoding HRAB. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HRAB, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on HRAB is preferred, but a competitive binding assay may be employed. These and other assays are described, among other places, in Hampton et al. (1990; *Serological Methods, a Laboratory Manual,* APS Press, St Paul, Minn.) and Maddox et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HRAB include oligolabeling, nick translation, end-labeling or PCR amplification using a labeled nucleotide. Alternatively, the sequence encoding HRAB, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn (Kalamazoo, Mich.); Promega (Madison, Wis.); and U.S. Biochemical Corp. Cleveland, Ohio)). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HRAB may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HRAB may be designed to contain signal sequences which direct secretion of HRAB through a prokaryotic or eukaryotic cell membrane. Other recombinant constructions may be used to join sequences encoding HRAB to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HRAB may be used to facilitate purification. One such expression vector provides for expression of a fusion protein containing HRAB] and a nucleic acid encoding 6 histidine residues followed by thioredoxin and an enterokinase cleavage site. The histidine residues facilitate purification on IMIAC (immobilized metal ion affinity chromatography) as described in Porath J et al. (1992, Prot. Exp. Purif. 3: 263–281) while the enterokinase cleavage site provides a means for purifying HRAB from the fusion protein. A discussion of vectors which contain fusion proteins is provided in Kroll, D. J. et al. (1993; DNA Cell Biol. 12:441–453).

In addition to recombinant production, fragments of HRAB may be produced by direct peptide synthesis using solid-phase techniques (cf Stewart et al. (1969) *Solid-Phase Peptide Synthesis,* W. H. Freeman Co., San Francisco, Calif.; Merrifield J. (1963) J. Am. Chem. Soc. 85:2149–2154). In vitro protein synthesis may be performed using manual techniques or by automation. Automated synthesis may be achieved, for example, using an Applied Biosystems 431A peptide synthesizer (Perkin Elmer). Various fragments of HRAB may be chemically synthesized separately and combined using chemical methods to produce the full length molecule

THERAPEUTICS

In another embodiment of the invention, HRAB or fragments thereof may be used for therapeutic purposes.

Chemical and structural homology exists among HRAB proteins, canine rab22 (GI 437987; SEQ ID NO:9), rat Rab-related GTP-binding protein (GI 206543; SEQ ID NO:10), mouse Rab17 (GI 297157; SEQ ID NO:11), and mouse Rab6/Rab5-associated protein (GI 722667; SEQ ID NO:12).

From the homology information provided above, it appears that HRAB play a role in intracellular transport. Accordingly, in another embodiment of the invention, HRAB or derivatives thereof, may be used to treat choroideremia, AIDS, and cancer.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HRAB or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HRAB have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HRAB amino acids may be fused with those of another protein such as keyhole limpet hemocyanin and antibody produced against the chimeric molecule.

Monoclonal antibodies to HRAB may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy,* Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HRAB-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, et al. (1989) Proc. Natl. Acad. Sci. 86: 3833–3837; Winter, G. et al. (1991) Nature 349:293–299).

Antibody fragments which contain specific binding sites for HRAB may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HRAB and its specific antibody. A two-site, monoclonal-based immunoassay utilizing monoclonal antibodies reactive to two non-interfering HRAB epitopes is preferred, but a competitive binding assay may also be employed (Maddox, supra).

In another embodiment of the invention, the polynucleotides encoding HRAB, or any fragment thereof, or antisense sequences, may be used for therapeutic purposes. In one aspect, antisense to the polynucleotide encoding HRAB may be used in situations in which it would be desirable to block the synthesis of the protein. In particular, cells may be transformed with sequences complementary to polynucleotides encoding HRAB. Thus, antisense sequences may be used to modulate HRAB activity, or to achieve regulation of gene function. Such technology is now well known in the art, and sense or antisense oligomers or larger fragments, can be designed from various locations along the coding or control regions of sequences encoding HRAB.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HRAB. These techniques are described both in Sambrook et al. (supra) and in Ausubel et al. (supra).

Genes encoding HRAB can be turned off by transforming a cell or tissue with expression vectors which express high levels of a polynucleotide or fragment thereof which encodes HRAB. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HRAB, i.e., the promoters, enhancers, and introns. Oligonucleotides derived from the transcription initiation site, e.g., between positions −10 and +10 from the ATG start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HRAB.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HRAB. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro . and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HRAB, antibodies to HRAB, mimetics, agonists, antagonists, or inhibitors of HRAB. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HRAB, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HRAB or fragments thereof, antibodies of HRAB, agonists, antagonists or inhibitors of HRAB, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HRAB may be used for the diagnosis of conditions or diseases characterized by expression of HRAB, or in assays to monitor patients being treated with HRAB, agonists, antagonists or inhibitors. The antibodies useful for diagnostic purposes may be prepared in the same manner as those described above for therapeutics. Diagnostic assays for HRAB include methods which utilize the antibody and a label to detect HRAB in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HRAB are known in the art and provide a basis for diagnosing altered or abnormal levels of HRAB expression. Normal or standard values for HRAB expression are established by combining body fluids or cell extracts taken from normal mammalian subjects, preferably human, with antibody to HRAB under conditions suitable for complex formation. The amount of standard complex formation may be quantified by various methods, preferably by photometric means. Quantities of HRAB expressed in subject, samples from biopsied tissues are compared with the standard values. Deviation between standard and subject values establishes the parameters for diagnosing disease.

In another embodiment of the invention, the polynucleotides encoding HRAB may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HRAB may be correlated with disease. The diagnostic assay may be used to distinguish between absence, presence, and excess expression of HRAB, and to monitor regulation of HRAB levels during therapeutic intervention.

In one aspect, hybridization with PCR probes which are capable of detecting polynucleotide sequences, including genomic sequences, encoding HRAB or closely related molecules, may be used to identify nucleic acid sequences which encode HRAB. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HRAB, alleles, or related sequences.

Probes may also be used for the detection of related sequences, and should preferably contain at least 50% of the nucleotides from any of the HRAB encoding sequences. The hybridization probes of the subject invention may be DNA or RNA and derived from the nucleotide sequence of SEQ ID NO:2, 4, 6, or 8 or from genomic sequence including promoter, enhancer elements, and introns of the naturally occurring HRAB.

Means for producing specific hybridization probes for DNAs encoding HRAB include the cloning of nucleic acid sequences encoding HRAB or HRAB derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HRAB may be used for the diagnosis of choroideremia, AIDS, and cancer. The polynucleotide sequences encoding HRAB may be used in Southern or northern analysis, dot blot, or other membrane-based technologies; in PCR technologies; or in dip stick, pin, ELISA or chip assays utilizing fluids or tissues from patient biopsies to detect altered HRAB expression. Such qualitative or quantitative methods are well known in the art.

In a particular aspect, the nucleotide sequences encoding HRAB may be useful in assays that detect activation or induction of various cancers, particularly those mentioned above. The nucleotide sequence encoding HRAB may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HRAB in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HRAB, a normal or standard profile for expression is established. This may be accomplished by combining body fluids or cell extracts taken from normal subjects, either animal or human, with a sequence, or a fragment thereof, which encodes HRAB, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides encoding HRAB may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HRAB include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequence which encodes HRAB may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in the 1994 Genome Issue of Science (265:1981 f). Correlation between the location of the gene encoding HRAB on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HRAB, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HRAB and the agent being tested, may be measured.

Another technique for drug screening which may be used provides for high throughput screening of compounds having suitable binding affinity to the protein of interest as described in published PCT application WO84/03564. In this method, as applied to HRAB large numbers of different small test compounds are synthesized on a solid substrate, such as plastic pins or some other surface. The test compounds are reacted with HRAB, or fragments thereof, and washed. Bound HRAB is then detected by methods well known in the art. Purified HRAB can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HRAB specifically compete with a test compound for binding HRAB. In this manner, the antibodies can be used to detect the presence of any peptide which shares one or more antigenic determinants with HRAB.

In additional embodiments, the nucleotide sequences which encode HRAB may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I Construction of cDNA Libraries
SYNORAB01 and SYNORAT01

The CDNA libraries for SYNORAB01 and SYNORAT01 were constructed from total RNA from the synovium of a rheumatoid elbow. The rheumatoid synovial tissue was obtained from UC Davis (lot #48) where it had been removed from a 51 year old Asian female and frozen. The frozen tissue was ground in a mortar and pestle and lysed immediately in a buffer containing guanidinium isothiocyanate. The lysate was extracted twice with phenol chloroform at pH 8.0 and centrifuged over a CsCl cushion using an SW28 rotor in an L8-70M ultracentrifuge (Beckman Instruments). The RNA was precipitated using 0.3M sodium acetate and 2.5 volumes of ethanol and resuspended in water.

The RNA for SYNORAB01 which was not DNase treated was used in the SUPERSCRIPT plasmid system for cDNA synthesis and plasmid cloning (catalogue #18248-013; Gibco BRL, Gaithersburg Md.) with the recommended protocol. cDNAs were fractionated on a SEPHAROSE CL4B column (catalog #275105, Pharmacia, and those cDNAs exceeding 1 kb were ligated into PSPORT1. The plasmid was transformed into chemically competent DH5α host cells (Gibco BRL).

The RNA for SYNORAT01 was DNase treated for 15 min at 37° C. before library construction. First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on SEPHACRYL S400 to obtain sequences which exceeded 1000 bp in size. The size selected cDNAs were inserted into the LAMBDAZAP vector system (Stratagene); and the vector, which contains the BLUESCRIPT phagemid (Stratagene), was transformed into cells of E. coli, strain XL1-BLUEMRF™ (Stratagene).

In SYNORAT01, the plasmid forms of individual cDNA clones were obtained by the in vivo excision process. Enzymes from both pBluescript and a cotransformed fl helper phage nicked the DNA, initiated new DNA synthesis, and created the smaller, singlestranded circular phagemid DNA molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

EOSIHET02

The eosinophils used for this library were obtained via aphoresis of a 56 year old Caucasian male patient who had been diagnosed with hypereosinophilic syndrome. The cells were washed twice in phosphate buffered saline and lysed immediately in a buffer containing guanidinium isothiocyanate. The lysate was extracted twice with phenol chloroform and centrifuged over a CsCl cushion using an SW28 rotor and an L8-70M ultracentrifuge (Beckman Instruments). The RNA was precipitated using 0.3M sodium acetate and 2.5 volumes of ethanol, resuspended in water and DNase treated for 15 min at 37° C. The RNA was isolated using the QIAGEN OLIGOTEX kit (QIAGEN Inc, Chatsworth Calif.) and sent to Stratagene for the construction of a custom cDNA library.

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LAMBDAZAP vector system (Stratagene); then the vector which contains the BLUESCRIPT phagemid (Stratagene) was transformed into E. coli host cells strain XL1-BlueMRF™ (Stratagene).

The phagemid forms of individual cDNA clones were obtained by the in vivo excision process. Enzymes from both BLUESCRIPT and a cotransformed fl helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

TESTTUT02

The TESTTUT02 cDNA library was constructed from testicle tumor tissue obtained from a 31-year old Caucasian male by unilateral orchiectomy. The pathology report indicated that tumor was identified at the spermatic cord region, and rare foci of residual testicle showed intralobular germ cell neoplasia. Initially, the patient presented with backache. The patient also had a history of tobacco use. The patient was taking COLACE (ocusate sodium; Roberts Pharmaceutical Corp., Eatontown, N.J.) and antacids at the time of surgery.

The frozen tissue was homogenized and lysed using a Polytron PT-3000 (Brinkmann Instruments, Westbury, N.J.) in guanidinium isothiocyanate solution. The lysate was centrifuged over a 5.7M CsCl cushion using an SW28 rotor in an L8-70M Ultracentrifuge (Beckman Instruments) for 18 hours at 25,000 rpm at ambient temperature. The RNA was extracted with acid phenol pH 4.0, precipitated using 0.4M sodium acetate and 2.5 volumes of ethanol, resuspended in RNAse-free water, and DNase treated at 37° C. The RNA extraction was repeated with acid phenol pH 4.0 and precipitated with sodium acetate and ethanol as before. The mRNA was then isolated using the QIAGEN OLIGOTEX RNA isolation kit (QIAGEN Inc.) and used to construct the cDNA library.

The mRNA was handled according to the recommended protocols in the SUPERSCRIPT plasmid system for cDNA synthesis and plasmid cloning (Catalog #18248-013, Gibco/BRL). The commercial plasmid PSPORT1 (Gibco/BRL) was digested with EcoRI restriction enzyme (New England Biolabs, Beverley, Mass.). The overhanging ends of the plasmid were filled in using Klenow enzyme (New England Biolabs) and 2'-deoxynucleotide 5'-triphosphates (dNTPs). The plasmid was self-ligated and transformed into the bacterial host, E. coli strain JM 109. An intermediate plasmid produced by the bacteria failed to digest with EcoR I confirming the desired loss of the EcoR I restriction site.

This intermediate plasmid (PSPORT1-ΔRI) was then digested with Hind III restriction enzyme (New England Biolabs) and the overhang was filled in with Klenow and dNTPs. A IO-mer linker of sequence 5'...CGGAATTCCG...3' was phosphorylated and ligated onto the blunt ends. The product of the ligation reaction was digested with EcoR I and self-ligated. Following transformation into JM109 host cells, plasmids were isolated and screened for the digestibility with EcoR I but not with Hind III. A single colony which met this criteria was designated pINCY 1. The plasmid produced by this colony was sequenced and found to contain several copies of the IO-mer linker. These extra linkers did not present a problem as they were eliminated when the vector was prepared for cloning.

The plasmid was tested for its ability to incorporate cDNAs from a library prepared using Not I and EcoR I restriction enzymes. Several clones were sequenced and a single clone containing an insert of approximately 0.8 kb was selected to prepare a large quantity of the plasmid for library production. After digestion with Not I and EcoR I, the plasmid and the CDNA insert were isolated on an agarose gel and the vector was purified on a QIAQUICK (QIAGEN, Inc.) column for use in library construction.

cDNAs were fractionated on a SEPHAROSE CL4B column (Catalog #275105-01, Pharmacia), and those cDNAs exceeding 400 bp were ligated into PSPORT1. The plasmid library in PSPORT1 was subsequently transformed into DH5α competent cells (Cat. #18258-012, Gibco/BRL).

II Isolation and Sequencing of cDNA Clones
SYNORAB01 and SYNORAT01

Plasmid DNA was purified using the Miniprep kit (Catalogue #77468, Advanced Genetic Technologies Corporation, Gaithersburg Md.), a 96-well block kit with reagents for 960 purifications. The recommended protocol included with the kit was employed except for the following changes. Each of the 96 wells was filled with only 1 ml of sterile Terrific Broth (Catalog #22711, LIFE TECHNOLOGIES, Gaithersburg Md.) with carbenicillin at 25 mg/L and glycerol at 0.4%. After the wells were inoculated, the bacteria were cultured for 24 hours and lysed with 60 µl of lysis buffer. A centrifugation step (Beckman GS-6R @2900 rpm for 5 min; Beckman Instruments) was performed before the contents of the block were added to the primary filter plate. The optional step of adding isopropanol to TRIS buffer was not routinely performed. After the last step in the protocol, samples were transferred to a Beckman 96-well block for storage.

EOSIHET02

Plasmid DNA was released from the cells and purified using the Miniprep kit (Catalogue #77468; Advanced Genetic Technologies Corporation, Gaithersburg Md.) as descrubed above.

Alternative methods of purifying plasmid DNA include the use of MAGIC MINIPREPS DNA purification system (Catalogue #A7100, Promega, Madison Wis.) or QIAwell™-8 Plasmid, QIAwell PLUS™ DNA and QIAWELL-8 plasmid, QIAWELL PLUS DNA, and QIAWELL ULTRA DNA purification systems (QIAGEN).

TESTTUT02

Plasmid DNA was released from the cells and purified using the R.E.A.L. PREP 96 plasmid kit for rapid extraction alkaline lysis plasmid minipreps (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, LIFE TECHNOLOGIES) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a MICROLAB 2200 (Hamilton, Reno, Nev.) in combination with Peltier thermal cyclers (PTC200 from MJ Research, Watertown, Mass.) and Applied Biosystems 377 DNA sequencing systems, and the reading frame was determined.

Most of the sequences disclosed herein were sequenced according to standard ABI protocols, using ABI kits (Cat. Nos. 79345, 79339, 79340, 79357, 79355). The solution volumes were used at 0.25x–1.0x concentrations. Some of the sequences disclosed herein were sequenced using different solutions and dyes which, unless otherwise noted, came from Amersham Life Science (Cleveland, Ohio).

First, stock solutions were prepared with HPLC water. The following solutions were each mixed by vortexing for 2 min: 1) Tris-EDTA (TE) Buffer was prepared by adding 49 ml water to 1 ml 50x Tris-EDTA concentrate, and 2) 10% Reaction Buffer was prepared by adding 45 ml water to 5 ml Concentrated Thermo Sequenase (TS) Reaction Buffer.

Second, 0.2 µM energy transfer (ET) primers were prepared in the following manner. Each primer tube was centrifuged prior to opening to assure that all primer powder was on the bottom of the tube. After each solubilization step, the mixture was vortexed for 2 min and then centrifuged for about 10 sec in a table-top centrifuge. 1 ml of 1x TE was added to each primer powder; adenine and cytosine dissolved primers (5-carboxyrhodamine-6G (R6G) and 6-carboxyfluorescein (FAM), respectively), were diluted with 9 ml 1x TE. Guanine and thymine dyes (N,N,N',N"-tetramethyl-6-carboxyrhodamine (TAM) and 6-carboxy-X-rhodamine (ROX), respectively) were diluted with 19 ml 1x TE.

Next, the sequencing reaction ready mix was prepared as follows: 1) nucleotides A and C (8 ml of each) were added to 6 ml ET primer and 18 ml TS reaction buffer; and 2) nucleotides G and T (8 ml of each) were added to 6 ml ET primer and 18 ml TS reaction buffer.

After vortexing for 2 min and centrifuging for 20 sec, the resulting solution was divided into tubes in volumes of 8 ml per tube in order to make 1x (A,C) and 2x (G,T) solutions.

After thermal cycling, the A, C, G, and T reactions with each DNA template were combined. Then, 50 µL 100% ethanol was added and the solution was spun at 4° C. for 30 min. The supernatant was decanted and the pellet was rinsed with 100 µL 70% ethanol. After being spun for 15 min the supernatant was discarded and the pellet was dried for 15 min under vacuum. The DNA sample was dissolved in 3 µL of formamide/50 mM EDTA. The resulting samples were loaded on wells in volumes of 2 µL per well for sequencing in ABI sequencers.

III Homology Searching of cDNA Clones and
Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S.F. 1993 and 1990, supra) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity x% maximum BLAST score 100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HRAB occurs. Abundance and percent abundance are also reported. Abundance directly reflects the number of times a particular transcript is represented in a cDNA library, and percent abundance is abundance divided by the total number of sequences examined in the cDNA library.

V Extension of HRAB-Encoding Polynucleotides to Full Length or to Recover Regulatory Sequences Full length HRAB-encoding nucleic acid sequence (SEQ ID NO:2, 4, 6, or 8) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier thermal cycler (PTC200; M. J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 µl of liquid LB/2x Carb medium placed in an individual well of an appropriate, commercially-available, sterile 96-well microtiter plate. The following day, 5 µl of each overnight culture is transferred into a non-sterile 96-well plate and after dilution 1:10 with water, 5 μl of each sample is transferred into a PCR array.

For PCR amplification, 18 μl of concentrated PCR reaction mix (3.3x) containing 4 units of rTth DNA polymerase, a vector primer, and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2, 4, 6, or 8 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 software (National Biosciences), labeled by combining 50 pmol of each oligomer and 250 mCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR film (Kodak, Rochester, N.Y.) is exposed to the or the blots are exposed to in a Phosphoimager cassette (Molecular Dynamics, Sunnyvale, Calif.), hybridization patterns are compared visually.

VII Antisense Molecules

Antisense molecules to the HRAB-encoding sequence, or any part thereof, is used to inhibit in vivo or in vitro expression of naturally occurring HRAB. Although use of antisense oligonucleotides, comprising about 20 base-pairs, is specifically described, essentially the same procedure is used with larger cDNA fragments. An oligonucleotide based on the coding sequences of HRAB, as shown in FIGS. 1A, 1B, and 1C is used to inhibit expression of naturally occurring HRAB. The complementary oligonucleotide is designed from the most unique 5' sequence as shown in FIGS. 1A, 1B, and 1C and used either to inhibit transcription by preventing promoter binding to the upstream nontranslated sequence or translation of an HRAB-encoding transcript by preventing the ribosome from binding. Using an appropriate portion of the signal and 5' sequence of SEQ ID NO:2, 4, 6, or 8, an effective antisense oligonucleotide includes any 15–20 nucleotides spanning the region which translates into the signal or 5' coding sequence of the polypeptide as shown in FIGS. 1A, 1B, and 1C.

VIII Expression of HRAB

Expression of HRAB is accomplished by subcloning the cDNAs into appropriate vectors and transforming the vectors into host cells. In this case, the cloning vector, PSPORT, previously used for the generation of the cDNA library is used to express HRAB in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HRAB into the bacterial growth media which can be used directly in the following assay for activity.

IX Demonstration of HRAB Activity

HRAB's GTP binding activity can be assayed by a technique described by Brauers A et al (1996, Eur J Biochem 237: 833–840). Samples of 10 ug HRAB are incubated with tracer $^{35}$S guanosine 5'-O-[gamma-thio] triphosphate ([$^{35}$S] GTP[S]; 300,000 cpm/sample) in a buffer containing 20 mM $MgCl_2$, 1 mM dithiotlreitol and 0.1% Triton X-100 in a total volume of 100 ml. Unlabeled GTP[S] is added and the binding is allowed to proceed at 30° C. for 1 hour. The reaction is terminated by addition of 1 ml ice-cold buffer containing 20 mM Tris, pH 8.0, 100 mM NaCl and 25 mM $MgCl_2$. The samples are filtered through nitrocellulose membranes and washed four times with 1 ml buffer. Samples are placed in scintillation cocktail and radioactivity is measured by scintillation counting.

X Production of HRAB Specific Antibodies

HRAB that is substantially purified using PAGE electrophoresis (Sambrook, supra), or other purification techniques, is used to immunize rabbits and to produce antibodies using standard protocols. The amino acid sequence deduced from SEQ ID NO:2, 4, 6, or 8 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems 431A peptide synthesizer using fmoc-chemistry, and coupled to keyhole limpet hemocyanin (KLH, Sigma) by reaction with M-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1%

BSA, reacting with rabbit antisera, washing, and reacting with radioiodinated, goat anti-rabbit IgG.

XI Purification of Naturally Occurring HRAB Using Specific Antibodies

Naturally occurring or recombinant HRAB is substantially purified by immunoaffinity chromatography using antibodies specific for HRAB. An immunoaffinity column is constructed by covalently coupling HRAB antibody to an activated chromatographic resin, such as CnBr-activated Sepharose (Pharmacia & Upjohn). After the coupling, the resin is blocked and washed according to the manufacturer's instructions.

Media containing HRAB is passed over the immunoaffinity column, and the column is washed under -continued Ile Glu Glu Leu Phe Gln Gly Ile Ser Arg Gln Ile Pro Pro Leu Asp
145                 150                 155                 160

Pro His Glu Asn Gly Asn Asn Gly Thr Ile Lys Val Glu Lys Pro Thr
            165                 170                 175

Met Gln Ala Ser Arg Arg Cys Cys
        180

(2) INFORMATION FOR SEQ ID NO:2:

(i) SEQUENCE CHARACTERISTICS:
        (A) LENGTH: 848 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

CGCTTTGNTC CGTTTANCCC GGTTCAGANG NGCCGCTGAG CTCCGGCACT GCCTGGCTGC      60

GAGCACATGA TGGCGATACG GGAGCTCAAA GTGTGCCTTC TCGGGGGACT GATGGAACCG     120

ATCTGTTCCC TTACGAAGTG TCACAGTATT GGCAGGACTC TGGACAAGGA CAAGGAAGGC     180

TGCATTCCTG TGGCACCACC AGGTGGAAGA TGGAGGACAC TGGGGTTGGG AAATCAAGCA     240

TCGTGTGTCG ATTTGTCCAG GATCACTTTG ACCACAACAT CAGCCCTACT ATTGGGGCAT     300

CTTTTATGAC CAAAACTGTG CCTTGTGGAA ATGAACTTCA CAAGTTCCTC ATCTGGGACA     360

CTGCTGGTCA GGAACGGTTT CATTCATTGG CTCCCATGTA CTATCGAGGC TCAGCTGCAG     420

CTGTTATCGT GTATGATATT ACCAAGCAGG ATTCATTTTA TACCTTGAAG AAATGGGTCA     480

AGGAGCTGAA AGAACATGGT CCAGAAAACA TTGTAATGGC CATCGCTGGA AACAAGTGCG     540

ACCTCTCAGA TATTAGGGAG GTTCCCCTGA AGGATGCTAA GGAATACGCT GAATCCATAG     600

GTGCCATCGT GGTTGAGACA AGTGCAAAAA ATGCTATTAA TATCGAAGAG CTCTTTCAAG     660

GAATCAGCCG CCAGATCCCA CCCTTGGACC CCATGAAAAA TGGAAACAAT GGAACAATCA     720

AAGTTGAGAA GCCAACCATG CAAGCCAGCC GCCGGTGCTG TTGACCCAAG GCCCGTGGTC     780

CACGGTACTT GAAGAAGCCA GAGCCCACAT CCTGTGCACT GCTGAAGGAC CCTACNGCTC     840

GGTGGCCT                                                              848

(2) INFORMATION FOR SEQ ID NO:3:

(i) SEQUENCE CHARACTERISTICS:
        (A) LENGTH: 209 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:3:

Met Gln Ala Pro His Lys Glu His Leu Tyr Lys Leu Leu Val Ile Gly
1               5                   10                  15

Asp Leu Gly Val Gly Lys Thr Ser Ile Ile Lys Arg Tyr Val His Gln
            20                  25                  30

```
Leu Phe Ser Gln His Tyr Arg Ala Thr Ile Gly Val Asp Phe Ala Leu
         35                  40                  45

Lys Val Leu Asn Trp Asp Ser Arg Thr Leu Val Arg Leu Gln Leu Trp
 50                  55                  60

Asp Ile Ala Gly Gln Glu Arg Phe Gly Asn Met Thr Arg Val Tyr Tyr
 65                  70                  75                  80

Lys Glu Ala Val Gly Ala Phe Val Val Phe Asp Ile Ser Arg Ser Ser
                 85                  90                  95

Thr Phe Glu Ala Val Leu Lys Trp Lys Ser Asp Leu Asp Ser Lys Val
                100                 105                 110

His Leu Pro Asn Gly Ser Pro Ile Pro Ala Val Leu Leu Ala Asn Lys
            115                 120                 125

Cys Asp Gln Asn Lys Asp Ser Ser Gln Ser Pro Ser Gln Val Asp Gln
130                 135                 140

Phe Cys Lys Glu His Gly Phe Ala Gly Trp Phe Glu Thr Ser Ala Lys
145                 150                 155                 160

Asp Asn Ile Asn Ile Glu Glu Ala Ala Arg Phe Leu Val Glu Lys Ile
                165                 170                 175

Leu Val Asn His Gln Ser Phe Pro Asn Glu Glu Asn Asp Val Asp Lys
                180                 185                 190

Ile Lys Leu Asp Gln Glu Thr Leu Arg Ala Glu Asn Lys Ser Gln Cys
            195                 200                 205

Cys
```

(2) INFORMATION FOR SEQ ID NO:4:

(i) SEQUENCE CHARACTERISTICS:
        (A) LENGTH: 890 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:4:

```
GGCTGCGCTT CCCTGGTCAG GCACGGCACG TCTGGCCGGC CGCCAGGATG CAGGCCCCGC    60

ACAAGGAGCA CCTGTACAAG TTGCTGGTGA TTGGCGACCT GGGCGTGGGS AAGACCAGYA   120

TCATCAAGCG CTACGTCCAC CAGCTCTTCT CCCAGCACTA CCGGGCCACC ATCGGGGTGG   180

ACTTCGCCCT CAAGGTCCTC AACTGGGACA GCAGGACTCT GGTGCGCCTG CAGCTGTGGG   240

ACATCGCGGG GCAGGAGCGA TTTGGCAACA TGACCCGAGT ATACTACAAG GAAGCTGTTG   300

GTGCTTTTGT AGTCTTTGAT ATATCAAGAA GTTCCACATT TGAGGCAGTC TTAAAATGGA   360

AAAGTGATCT GGATAGTAAA GTTCATCTTC CAAATGGCAG CCCTATCCCT GCTGTCCTCT   420

TGGCTAACAA ATGTGACCAG AACAAGGACA GTAGCCAGAG TCCTTCCCAG GTGGACCAAT   480

TCTGCAAAGA ACATGGCTTT GCCGGATGGT TTGAAACCTC TGCAAAGGAT AACATAAACA   540

TAGAGGAAGC TGCCCGGTTC CTAGTGGAGA AGATTCTTGT AAACCACCAA AGCTTTCCTA   600

ATGAAGAAAA CGATGTGGAC AAAATTAAGC TAGATCAAGA GACCTTGAGA GCAGAGAACA   660

AATCCCAGTG TTGCTGATAT ATGGCTTCTG CTTCTCTTGT GTGTGCCTCA GCTCTGAAGA   720

AGTTCCTGAG AATGGGTTAC AGATGTCATG TNAGCTGGGA GTCTTCCNAC ATGTGGNACT   780

TCAAAAGGCA GCACNACTGG GCGCNTGCAC TTATTTGAAA ATGGAACTTT GGGAGAAGTA   840
```

TCCCTGCTAN TGGCTCTGTA ACTTAACAGA TGACAATTAG GCTTTTGTNA                    890

(2) INFORMATION FOR SEQ ID NO:5:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: peptide (iii) HYPOTHETICAL: NO (vii) IMMEDIATE SOURCE:
        (A) LIBRARY:
        (B) CLONE: Consensus (xi) SEQUENCE DESCRIPTION: SEQ ID NO:5:

```
Met Ala Gln Ala His Arg Thr Pro Gln Pro Arg Ala Ala Pro Ser Gln
 1               5                  10                  15

Pro Arg Val Phe Lys Leu Val Leu Leu Gly Ser Gly Ser Val Gly Ala
                20                  25                  30

Phe Phe Thr Lys Glu Val Asp Val Gly Ala Thr Ser Leu Lys Leu Glu
            35                  40                  45

Ile Trp Asp Thr Ala Gly Gln Glu Lys Tyr His Ser Val Cys His Leu
50                      55                  60

Tyr Phe Arg Gly Ala Asn Ala Ala Leu Leu Val Tyr Asp Ile Thr Arg
65                  70                  75                  80

Lys Asp Ser Phe Leu Lys Ala Gln Gln Trp Leu Lys Asp Leu Glu Glu
                85                  90                  95

Glu Leu His Pro Gly Glu Val Leu Val Met Leu Val Gly Asn Lys Thr
            100                 105                 110

Asp Leu Ser Gln Glu Arg Glu Val Thr Phe Gln Glu Gly Lys Glu Phe
        115                 120                 125

Ala Asp Ser Gln Lys Leu Leu Phe Met Glu Thr Ser Ala Lys Leu Asn
130                 135                 140

His Gln Val Ser Glu Val Phe Asn Thr Val Ala Gln Glu Leu Leu Gln
145                 150                 155                 160

Arg Ser Asp Glu Glu Gly Gln Ala Leu Arg Gly Asp Ala Ala Val Ala
                165                 170                 175

Leu Asn Lys Gly Pro Ala Arg Gln Ala Lys Cys Cys Ala His
            180                 185                 190
```

(2) INFORMATION FOR SEQ ID NO:6:

(i) SEQUENCE CHARACTERISTICS:
        (A) LENGTH: 820 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:6:

CTGCCTGCGG AGGGAAGCAA ACCTTCCCCT GGACCAGAGA GAGGAGAAAG CGGAGACAGG          60

TAGCAACGCT GTGGACTGGT GATGACAGGC TCTTCAGCTC CCTGCAAGTG ACCGGGCCTG         120

```
GGGAACAGGG CATGGCACAG GCACACAGGA CCCCCCAGCC CAGGGCTGCC CCCAGCCAGC      180

CCCGTGTGTT CAAGCTGGTT CTCCTGGGAA GTGGCTCCGT GGGTGCGTTC TTCACAAAGG      240

AGGTGGATGT GGGTGCCACC TCTCTGAAGC TTGAGATCTG GGACACAGCT GGCCAGGAGA      300

AGTACCACAG CGTCTGCCAC CTCTACTTCA GGGGTGCCAA CGCTGCGCTT CTGGTGTACG      360

ACATCACCAG GAAGGATTCC TTCCTCAAGG CTCAGCAGTG GCTGAAGGAC CTGGAGGAGG      420

AGCTGCACCC AGGAGAAGTC CTGGTGATGC TGGTGGGCAA CAAGACGGAC CTCAGCCAGG      480

AGCGGGAGGT GACCTTCCAG GAAGGGAAGG AGTTTGCCGA CAGCCAGAAG TTGCTGTTCA      540

TGGAAACTTC GGCCAAACTG AACCACCAGG TGTCGGAGGT GTTCAATACA GTGGCCCAAG      600

AGCTACTGCA GAAGCGAC GAGGAGGGCC AGGCTCTACG GGGGATGCA GCTGTGGCTC         660

TGAACAAGGG GCCCGCGAGG CAGGCCAAAT GCTGCGCCCA CTAGGTGCAG CCACTCCTGG      720

GGGCTGTGGG GAAGACANCC CCTGCCTGGG CCATGGCCAG CTCTAGGTGG ATTCTGATTC      780

ACTGTCAATG CTGGGTTGCT CCCGAGCCCT AGATGTTCCT                            820
```

(2) INFORMATION FOR SEQ ID NO:7:

(i) SEQUENCE CHARACTERISTICS:
        (A) LENGTH: 184 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:
        (B) CLONE: Consensus (xi) SEQUENCE DESCRIPTION: SEQ ID NO:7:

```
Met Ala Ala Gln Lys Asp Gln Gln Lys Asp Ala Glu Ala Glu Gly Leu
 1               5                  10                  15

Ser Gly Thr Thr Leu Leu Pro Lys Leu Ile Pro Ser Gly Ala Gly Arg
            20                  25                  30

Glu Trp Leu Glu Arg Arg Ala Thr Ile Arg Pro Gly Ala Pro Ser
        35                  40                  45

Trp Thr Ser Ser Ala Ser His Gly Pro Ala Thr Trp Glu Ser Cys Ala
 50                  55                  60

Ser Ala Val Arg Asn Val Glu Tyr Tyr Gln Ser Asn Tyr Val Phe Val
65                  70                  75                  80

Phe Leu Gly Leu Ile Leu Tyr Cys Val Val Thr Ser Pro Met Leu Leu
                85                  90                  95

Val Ala Leu Ala Val Phe Gly Ala Cys Tyr Ile Leu Tyr Leu Arg
            100                 105                 110

Thr Leu Glu Ser Lys Leu Val Leu Phe Gly Arg Glu Val Ser Pro Ala
        115                 120                 125

His Gln Tyr Ala Leu Ala Gly Gly Ile Ser Phe Pro Phe Trp Leu
    130                 135                 140

Ala Gly Ala Gly Ser Ala Val Phe Trp Val Leu Gly Ala Thr Leu Val
145                 150                 155                 160

Val Ile Gly Ser His Ala Ala Phe His Gln Ile Glu Ala Val Asp Gly
                165                 170                 175

Glu Glu Leu Gln Met Glu Pro Val
            180
```

(2) INFORMATION FOR SEQ ID NO:8:

(i) SEQUENCE CHARACTERISTICS:
       (A) LENGTH: 757 base pairs
       (B) TYPE: nucleic acid
       (C) STRANDEDNESS: single
       (D) TOPOLOGY: linear (ii) MOLECULE TYPE: cDNA (vii) IMMEDIATE SOURCE:
       (A) LIBRARY:
       (B) CLONE: Consensus (xi) SEQUENCE DESCRIPTION: SEQ ID NO:8:

```
GGGTACCGGG CTGGTTACAG CAGCTCTACC CCTCACGACG CAAACATGGC AGCGCAGAAG    60

GACCAGCAGA AAGATGCCGA GGCGGAAGGG CTGAGCGGCA CGACCCTGCT GCCGAAGCTG   120

ATTCCCTCCG GTGCAGGCCG GGAGTGGCTG GAGCGGCGCC GCGCGACCAT CCGCCCTGGA   180

GCACCTTCGT GGACCAGCAG CGCTTCTCAC GGCCCCGCAA CCTGGGAGAG CTGTGCCAGC   240

GCTGTACGCA ACGTGGAGTA CTACCAGAGC AACTATGTGT CGTGTTCCT GGGCCTCATC    300

CTGTACTGTG TGGTGACGTC CCCTATGTTG CTGGTGGCTC TGGCTGTCTT TTTCGGCGCC   360

TGTTACATTC TCTATCTGCG CACCTTGGAG TCCAAGCTTG TGCTCTTTGG CCGAGAGGTG   420

AGCCCAGCGC ATCAGTATGC TCTGGCTGGA GGCATCTCCT TCCCCTTCTT CTGGCTGGCT   480

GGTGCGGGCT CGGCCGTCTT CTGGGTGCTG GGAGCCACCC TGGTGGTCAT CGGCTCCCAC   540

GCTGCCTTCC ACCAGATTGA GGCTGTGGAC GGGGAGGAGC TGCAGATGGA ACCCGTGTGA   600

GGTGTCTTCT GGGACCTGCC GGCCTCCCGG GCCAGCTGCC CCACCCCTGC CCATGCCTGT   660

CCTGCACGGS TCTGCTGCTC GGGCCCACAG CGCCGTCCCA TCACAAGCCC GGGGAGGGAT   720

CCCGCCTTTR AAAATAAAGC TGTTATGGGT GTCATTC                            757
```

(2) INFORMATION FOR SEQ ID NO:9:

(i) SEQUENCE CHARACTERISTICS:
       (A) LENGTH: 194 amino acids
       (B) TYPE: amino acid
       (C) STRANDEDNESS: single
       (D) TOPOLOGY: linear (ii) MOLECULE TYPE: peptide (vii) IMMEDIATE SOURCE:
       (A) LIBRARY:GenBank
       (B) CLONE: 437987

(xi) SEQUENCE DESCRIPTION: SEQ ID NO:9:

```
Met Ala Leu Arg Glu Leu Lys Val Cys Leu Leu Gly Asp Thr Gly Val
 1               5                  10                  15

Gly Lys Ser Ser Ile Val Trp Arg Phe Val Glu Asp Ser Phe Asp Pro
                20                  25                  30

Asn Ile Asn Pro Thr Ile Gly Ala Ser Phe Met Thr Lys Thr Val Gln
             35                  40                  45

Tyr Gln Asn Glu Leu His Lys Phe Leu Ile Trp Asp Thr Ala Gly Gln
         50                  55                  60

Glu Ala Phe Arg Ala Leu Ala Pro Met Tyr Tyr Arg Gly Ser Ala Ala
 65                  70                  75                  80

Ala Ile Ile Val Tyr Asp Ile Thr Lys Glu Glu Thr Phe Ser Thr Leu
                 85                  90                  95

Lys Asn Trp Val Lys Glu Leu Arg Gln His Gly Pro Pro Asn Ile Val
            100                 105                 110
```

```
Val Ala Ile Ala Gly Asn Lys Cys Asp Leu Ile Asp Val Arg Glu Val
            115                 120                 125

Met Glu Arg Asp Ala Lys Asp Tyr Ala Asp Ser Ile His Ala Ile Phe
        130                 135                 140

Val Glu Thr Ser Ala Lys Asn Ala Ile Asn Ile Asn Glu Leu Phe Ile
145                 150                 155                 160

Glu Ile Ser Arg Arg Ile Pro Ser Ala Asp Ala Asn Pro Pro Ser Gly
                165                 170                 175

Gly Lys Gly Phe Lys Leu Arg Arg Gln Pro Ser Glu Pro Gln Arg Ser
            180                 185                 190

Cys Cys (2) INFORMATION FOR SEQ ID NO:10:

(i) SEQUENCE CHARACTERISTICS:
        (A) LENGTH: 211 amino acids
        (B) TYPE: amino acid
        (C) STRANDEDNESS: single
        (D) TOPOLOGY: linear (ii) MOLECULE TYPE: peptide (iii) HYPOTHETICAL: NO (vii) IMMEDIATE SOURCE:
        (A) LIBRARY:GenBank
        (B) CLONE: 206543

(xi) SEQUENCE DESCRIPTION: SEQ ID NO:10:

Met Gln Thr Pro His Lys Glu His Leu Tyr Lys Leu Val Ile Gly
1               5                  10                 15

Asp Leu Gly Val Gly Lys Thr Ser Ile Ile Lys Arg Tyr Val His Gln
            20                  25                  30

Asn Phe Ser Ser His Tyr Arg Ala Thr Ile Gly Val Asp Phe Ala Leu
        35                  40                  45

Lys Val Leu His Trp Asp Pro Glu Thr Val Val Arg Leu Gln Leu Trp
50                  55                  60

Asp Ile Ala Gly Gln Glu Arg Phe Gly Asn Met Thr Arg Val Tyr Tyr
65                  70                  75                  80

Arg Glu Ala Met Gly Ala Phe Ile Val Phe Asp Val Thr Arg Pro Ala
                85                  90                  95

Thr Phe Glu Ala Val Ala Lys Trp Lys Asn Asp Leu Asp Ser Lys Leu
            100                 105                 110

Thr Leu Pro Asn Gly Lys Pro Val Ser Val Leu Leu Ala Asn Lys
        115                 120                 125

Cys Asp Gln Gly Lys Asp Val Leu Val Asn Asn Gly Leu Lys Met Asp
130                 135                 140

Gln Phe Cys Lys Glu His Gly Phe Val Gly Trp Phe Glu Thr Ser Ala
145                 150                 155                 160

Lys Glu Asn Ile Asn Ile Asp Glu Ala Ser Arg Cys Leu Val Lys His
                165                 170                 175

Ile Leu Ala Asn Glu Cys Asp Phe Ile Glu Ser Ile Glu Pro Asp Ile
            180                 185                 190

Val Lys Pro His Leu Thr Ser Pro Lys Val Val Ser Cys Ser Gly Cys
        195                 200                 205

Ala Lys Ser
210
```

(2) INFORMATION FOR SEQ ID NO:11:

(i) SEQUENCE CHARACTERISTICS:
        (A) LENGTH: 214 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:GenBank
        (B) CLONE: 297157

(xi) SEQUENCE DESCRIPTION: SEQ ID NO:11:

```
Met Ala Gln Ala Ala Gly Leu Pro Gln Ala Ser Thr Ala Ser Gly Gln
 1               5                  10                  15

Pro Tyr Val Ser Lys Leu Val Leu Leu Gly Ser Ser Ser Val Gly Lys
                20                  25                  30

Thr Ser Leu Ala Leu Arg Tyr Met Lys Gln Asp Phe Ser Asn Val Leu
            35                  40                  45

Pro Thr Val Gly Cys Ala Phe Phe Thr Lys Val Leu Asp Leu Gly Ser
        50                  55                  60

Ser Ser Leu Lys Leu Glu Ile Trp Asp Thr Ala Gly Gln Glu Lys Tyr
65                  70                  75                  80

Gln Ser Val Cys His Leu Tyr Phe Arg Gly Ala Asn Ala Ala Leu Leu
                85                  90                  95

Val Tyr Asp Ile Thr Arg Lys Asp Ser Phe His Lys Ala Gln Gln Trp
            100                 105                 110

Leu Glu Asp Leu Glu Lys Glu Phe Gln Pro Gly Glu Val Val Val Met
        115                 120                 125

Leu Val Gly Asn Lys Thr Asp Leu Gly Glu Glu Arg Glu Val Thr Phe
130                 135                 140

Gln Glu Gly Lys Glu Phe Ala Glu Ser Lys Ser Leu Leu Phe Met Glu
145                 150                 155                 160

Thr Ser Ala Lys Leu Asn Tyr Gln Val Ser Glu Ile Phe Asn Thr Val
                165                 170                 175

Ala Gln Glu Leu Leu Gln Arg Ala Gly Asp Thr Gly Ser Ser Arg Pro
            180                 185                 190

Gln Glu Gly Glu Ala Val Ala Leu Asn Gln Glu Pro Pro Ile Arg Gln
        195                 200                 205

Arg Gln Cys Cys Ala Arg
        210
```

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY:GenBank
        (B) CLONE: 722667

(xi) SEQUENCE DESCRIPTION: SEQ ID NO:12:

```
His Glu Asp Gln Gln Lys Asp Ala Glu Gly Glu Gly Leu Ser Ala Thr
 1               5                  10                  15

Thr Leu Leu Pro Lys Leu Ile Pro Ser Gly Ala Gly Arg Glu Trp Leu
```

-continued

```
                20                      25                      30
Glu Gln Ala Pro Gly Asp His Pro Ala Leu Gly His Leu Ser Trp Thr
        35                  40                  45

Ser Asn Val Ser Arg Asp Pro Ala Met Trp Glu Ser Phe Ala Ser Ala
    50                  55                  60

Trp Tyr Gly Thr Val Glu Tyr Tyr Gln Ser Asn Tyr Val Phe Val Phe
65                  70                  75                      80

Leu Gly Leu Ile Leu Tyr Cys Val Val Thr Ser Pro Met Leu Leu Val
            85                  90                  95

Ala Leu Ala Val Phe Phe
            100
```

What is claimed is:

1. An isolated and purified polynucleotide sequence encoding a human Rab protein comprising the amino acid sequence of SEQ ID NO:1.

2. An isolated and purified full-length polynucleotide sequence which hybridizes under stringent wash conditions of 0.1X saline sodium citrate and 0.5% sodium dodecyl sulfate to the polynucleotide sequence of claim 1.

3. A hybridization probe comprising the polynucleotide sequence of claim 1.

4. An isolated and purified polynucleotide sequence consisting of SEQ ID NO:2.

5. An isolated and purified full-length polynucleotide sequence which is complementary to SEQ ID NO:2.

6. A hybridization probe comprising the polynucleotide sequence of claim 5.

7. An expression vector containing the polynucleotide sequence of claim 1.

8. A host cell containing the expression vector of claim 7.

9. A method for producing a polypeptide comprising the amino acid sequence of SEQ ID NO:1, the method comprising the steps of:

a) culturing the host cell of claim 8 under conditions suitable for the expression of the polypeptide; and b) recovering the polypeptide from the host cell culture.

* * * * *